United States Patent
Kubo et al.

(10) Patent No.: US 7,075,654 B2
(45) Date of Patent: Jul. 11, 2006

(54) MEASURING APPARATUS AND MEASURING CHIP

(75) Inventors: Takashi Kubo, Kaisei-machi (JP); Katsuaki Muraishi, Kaisei-machi (JP); Toshihito Kimura, Kaisei-machi (JP); Hitoshi Shimizu, Kaisei-machi (JP); Nobufumi Mori, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 11/256,151

(22) Filed: Oct. 24, 2005

(65) Prior Publication Data

US 2006/0039003 A1 Feb. 23, 2006

Related U.S. Application Data

(63) Continuation of application No. 10/102,203, filed on Mar. 21, 2002.

(30) Foreign Application Priority Data

| Mar. 22, 2001 | (JP) | ............................ 2001-081967 |
| Mar. 22, 2001 | (JP) | ............................ 2001-081968 |
| Dec. 27, 2001 | (JP) | ............................ 2001-397411 |

(51) Int. Cl.
  *G01N 21/55* (2006.01)
  *G01N 21/01* (2006.01)

(52) U.S. Cl. ..................... 356/445; 356/244

(58) Field of Classification Search ................. None
See application file for complete search history.

(56) References Cited

U.S. PATENT DOCUMENTS

| 5,313,264 A | 5/1994 | Ivarsson et al. |
| 5,485,277 A | 1/1996 | Foster |
| 5,822,073 A | 10/1998 | Yee et al. |
| 5,917,607 A | 6/1999 | Naya |
| 5,991,048 A | 11/1999 | Karlson et al. |
| 2001/0030751 A1 | 10/2001 | Bartholomew et al. |

FOREIGN PATENT DOCUMENTS

JP 61-226644 10/1986

(Continued)

OTHER PUBLICATIONS

Takayuki Okamoto, "Spectral Researches" vol. 47, No. 1, 1998, pp. 21-23 and 26-27.

*Primary Examiner*—Michael P. Stafira
(74) *Attorney, Agent, or Firm*—Sughrue Mion, PLLC

(57) ABSTRACT

Disclosed herein is a measuring apparatus equipped with a plurality of measuring units. Each measuring unit includes a dielectric block, a thin film layer formed on the dielectric block, and a sample holding mechanism for holding a sample on the thin film layer. The measuring apparatus is further equipped with an optical system for making a light beam enter the dielectric block at an angle of incidence so that a total internal reflection condition is satisfied at an interface between the dielectric block and the thin film layer, and photodetectors for measuring the intensity of the light beam totally reflected at the interface. The optical system is constructed so that light beams simultaneously enter the dielectric blocks of the measuring units. The number of photodetectors corresponds to the number of the light beams.

9 Claims, 25 Drawing Sheets

FOREIGN PATENT DOCUMENTS

| | | |
|---|---|---|
| JP | 6-167443 | 6/1994 |
| JP | 10-300667 | 11/1998 |
| JP | 11-153603 | 6/1999 |
| JP | 11-160317 | 6/1999 |
| JP | 2000-121552 | 4/2000 |
| JP | 2000-356585 | 12/2000 |
| JP | 2001-255267 | 9/2001 |
| WO | WO 90/05317 | 5/1990 |
| WO | WO 95/08774 | 3/1995 |
| WO | WO 95/22754 A | 8/1995 |
| WO | WO 00/31515 A | 6/2000 |

MEASURING APPARATUS AND MEASURING CHIP

This is a continuation of application Ser. No. 10/102,203 filed Mar. 21, 2002. The entire disclosure of the prior application, application Ser. No. 10/102,203 is hereby incorporated by reference.

BACKGROUND OF THE INVENTION

1. Field of the Invention

The present invention relates to a measuring apparatus, such as a surface plasmon resonance measuring apparatus, for analyzing a substance in a sample by utilizing the excitation of surface plasmon, and more particularly to a measuring apparatus for analyzing a substance in a sample, by making a light beam enter the interface between a thin film layer (or a metal film, or a cladding layer) in contact with the sample and a dielectric block so that the light beam is totally reflected at the interface, making an evanescent wave occur, and measuring a change in the intensity of the totally reflected light beam due to the evanescent wave. The invention also relates to a measuring chip that is employed in such a measuring apparatus.

2. Description of the Related Art

In metals, if free electrons are caused to vibrate in a group, a compression wave called a plasma wave will be generated. The compression wave, generated in the metal surface and quantized, is called surface plasmon.

There have hitherto been proposed various kinds of surface plasmon resonance measuring apparatuses for quantitatively analyzing a substance in a sample by taking advantage of a phenomenon that surface plasmon is excited by a light wave. Among such apparatuses, one employing a system called "Kretschmann configuration" is particularly well known (e.g., see Japanese Unexamined Patent Publication No. 6(1994)-167443).

The surface plasmon resonance measuring apparatus employing the "Kretschmann configuration" is equipped with a dielectric block formed, for example, into the shape of a prism; a metal film, formed on one surface of the dielectric block, for placing a sample thereon; and a light source for emitting a light beam. The measuring apparatus is further equipped with an optical system for making the light beam enter the dielectric block so that a condition for total internal reflection (TIR) is satisfied at the interface between the dielectric block and the metal film and that various angles of incidence, including a surface plasmon resonance condition, are obtained; and photodetection means for measuring the intensity of the light beam totally reflected at the interface, thereby detecting surface plasmon resonance.

To obtain various angles of incidence in the aforementioned manner, a relatively thin light beam can be deflected so that it strikes the above-mentioned interface at different angles of incidence, or a relatively thick beam can be convergently emitted so that the components thereof strike the interface at various angles of incidence. In the former, the light beam whose reflection angle varies with the deflection thereof can be detected by a small photodetector that is moved in synchronization with the light beam deflection, or by an area sensor extending along a direction where the reflection angle varies. In the latter, on the other hand, the light beams reflected at various angles can be detected by an area sensor extending in a direction where all the reflected light beams are received.

In the surface plasmon resonance measuring apparatus mentioned above, an evanescent wave having electric field distribution is generated in a sample in contact with the metal film, if a light beam strikes the metal film at a specific incidence angle $\theta_{sp}$ greater than a critical incidence angle at which total internal reflection (TIR) takes place. The generated evanescent wave excites surface plasmon at the interface between the metal film and the sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light satisfying TIR at the interface between the dielectric block and the metal film drops sharply. This sharp intensity drop is generally detected as a dark line by the above-mentioned photodetection means.

Note that the above-mentioned resonance occurs only when an incident light beam is a p-polarized light beam. Therefore, in order to make the resonance occur, it is necessary that a light beam be p-polarized before it strikes the interface.

If the wave number of the surface plasmon is found from the specific incidence angle $\theta_{sp}$ at which attenuated total reflection (ATR) takes place, the dielectric constant of a sample to be analyzed can be calculated by the following Equation:

$$K_{sp}(\omega) = (\omega/c)\{\epsilon_m(\omega)\epsilon_s\}^{1/2}/\{\epsilon_m(\omega)+\epsilon_s\}^{1/2}$$

where $K_{sp}$ represents the wave number of the surface plasmon, $\omega$ represents the angular frequency of the surface plasmon, $c$ represents the speed of light in vacuum, and $\epsilon_m$ and $\epsilon_s$ represent the dielectric constants of the metal and the sample, respectively.

If the dielectric constant $\epsilon_s$ of a sample is found, the density of a specific substance in the sample is found based on a predetermined calibration curve or the like. As a result, the specific substance in the sample can be quantitatively analyzed by finding the specific incidence angle $\theta_{sp}$ at which the intensity of the reflected light at the interface drops sharply.

In the conventional surface plasmon resonance measuring apparatus employing the aforementioned system, the metal film on which a sample is placed must be exchanged for a new one each time a measurement is made. Because of this, the metal film and the dielectric block are integrated into a single measuring unit (chip). After a measurement of each sample is made, each measuring unit is discarded (e.g., see Japanese patent application No. 2001-016633, filed by the present applicant)

As a similar sensor making use of ATR, there is known a leaky mode sensor (e.g., see "Spectral Researches," Vol. 47, No. 1 (1998), pp. 21 to 23 and pp. 26 to 27). This leaky mode sensor is equipped with a dielectric block formed, for example, into the shape of a prism; a cladding layer formed on one surface of the dielectric block; and an optical waveguide layer, formed on the cladding layer, for placing a sample thereon. The leaky mode sensor is further equipped with a light source for emitting a light beam; an optical system for making the light beam enter the dielectric block at various angles of incidence so that a condition for total internal reflection (TIR) is satisfied at the interface between the dielectric block and the cladding layer and so that ATR occurs by a waveguide mode excited in the optical waveguide layer; and photodetection means for measuring the intensity of the light beam totally reflected at the interface between the dielectric block and the cladding layer, and detecting the excited state of the waveguide mode, that is, ATR.

In the leaky mode sensor mentioned above, if a light beam strikes the cladding layer through the dielectric block at incidence angles greater than a critical incidence angle at which TIR takes place, the light beam is transmitted through the cladding layer and then only light with a specific wave number, incident at a specific incidence angle, propagates through the optical waveguide layer in a waveguide mode. If the waveguide mode is excited in this manner, the greater part of the incident light is confined within the optical waveguide layer, and consequently, ATR occurs in which the intensity of light totally reflected at the above-mentioned interface drops sharply. Since the wave number of the light propagating through the optical waveguide layer depends on the refractive index of a sample on the optical waveguide layer, both the refractive index of the sample and the properties of the sample related to the refractive index thereof can be analyzed by finding the above-mentioned specific incidence angle $\theta_{sp}$ at which ATR takes place.

In the case of the leaky mode sensor, as with the case of the aforementioned surface plasmon resonance measuring apparatus, the cladding layer and the optical waveguide layer can be fixed to the dielectric block and formed into a single measuring unit. After a measurement of each sample is made, each measuring unit can be discarded.

In the field of pharmaceutical manufacture and the like, the above-mentioned surface plasmon resonance measuring apparatus and leaky mode sensor are sometimes used in a random screening for detecting a specific substance that bonds with a predetermined sensing substance. In this case, the sensing substance is placed on the aforementioned thin film layer (i.e., the metal film in the case of the surface plasmon resonance measuring apparatus, or the cladding layer and optical waveguide layer in the case of the leaky mode sensor). Then, a liquid sample containing a target substance is dropped into the sensing substance, and each time a predetermined time elapses, the aforementioned specific incidence angle $\theta_{sp}$ is measured.

If the target substance in the liquid sample bonds with the sensing substance, the refractive index of the sensing substance varies with the lapse of time by the bond therebetween. Therefore, every time a predetermined time elapses, the specific incidence angle $\theta_{sp}$ is measured. Based on the measured value, the bond between the target substance and the sensing substance is measured. Next, based on the result, it can be judged whether or not the target substance is a specific substance that bonds with the sensing substance. An example of combination of the specific substance and the sensing substance is an antigen and an antibody. As an example of a measurement of such combination, there is a measurement of the bond between a human IgG (immunoglobulin G) antibody in a target substance and a rabbit antihuman IgG antibody (sensing substance).

Note that the specific incidence angle $\theta_{sp}$ at which ATR occurs itself does not always need to be detected to measure the bond between the target substance and the sensing substance. For example, a liquid sample is added to the sensing substance; then a change in the specific incidence angle $\theta_{sp}$ thereafter is measured; and based on the angle change, the bond can be measured.

However, a measuring apparatus, such as the aforementioned surface plasmon resonance sensor and leaky mode sensor, has the disadvantage that when measuring a plurality of samples, the measurement is extremely time-consuming. Particularly, in the case in which a single sample is measured several times at predetermined temporal intervals in order to detect a change in the properties of the sample due to an antigen-antibody reaction, a chemical reaction, etc., a new sample cannot be measured unless the measurement of the single sample is finished, and consequently, it takes too much time to measure all samples.

In addition, in the case where a conventional measuring chip such as that mentioned above is employed, it is fairly difficult to position the measuring chip accurately in a measuring apparatus such as a surface plasmon resonance measuring apparatus, etc. In the measuring apparatus utilizing ATR, to make high-precise measurements with good reproducibility, there is a need to make a light beam strike the interface between the dielectric block and the thin film layer (which is the metal film in the case of a measuring apparatus utilizing surface plasmon resonance, or the cladding layer in the case of a measuring apparatus utilizing the excitation of a waveguide mode) in a predetermined incidence angle range. However, if it is difficult to position the measuring chip precisely in the measuring apparatus, the incidence angle-range will vary, resulting in a reduction in accuracy of measurement. Furthermore, a conventional measuring chip such as that mentioned above is not convenient to handle. Because of this, it is difficult to make measurements efficiently.

SUMMARY OF THE INVENTION

The present invention has been made in view of the circumstances mentioned above. Accordingly, it is a first object of the present invention to provide a measuring apparatus which is capable of measuring a great number of samples in a short time. A second object of the invention is to provide a measuring chip that can be accurately positioned in a measuring apparatus such as a surface plasmon resonance measuring apparatus, etc. A third object of the invention is to provide a measuring chip that is convenient to handle.

In accordance with the present invention, there is provided a first measuring apparatus comprising:
    a plurality of measuring units comprising
    a dielectric block, a thin film layer formed on a surface of the dielectric block, and a sample holding mechanism for holding a sample on a surface of the thin film layer;
    a supporting body for supporting a plurality of measuring units;
    a light source for emitting a light beam;
    an optical incidence system for making the light beam enter the dielectric block at an angle of incidence so that a total internal reflection condition is satisfied at an interface between the dielectric block and the thin film layer; and
    photodetection means for measuring the intensity of the light beam totally reflected at the interface;
    wherein the optical system is constructed so that light beams simultaneously enter the dielectric blocks of at least two measuring units supported by the supporting body; and
    wherein the photodetection means comprises at least two photodetectors provided so that they correspond in number to the light beams which enter the dielectric blocks.

In accordance with the present invention, there is provided a second measuring apparatus comprising:
    a plurality of measuring units comprising
    a dielectric block, a thin film layer formed on a surface of the dielectric block, a sensing substance disposed on a surface of the thin film layer so that it interacts with a specific component in a sample, and a sample holding mechanism for holding the sample on a surface of the sensing substance;

a supporting body for supporting the plurality of measuring units;

a light source for emitting a light beam;

an optical incidence system for making the light beam enter the dielectric block at an angle of incidence so that a total internal reflection condition is satisfied at an interface between the dielectric block and the thin film layer; and photodetection means for measuring the intensity of the light beam totally reflected at the interface;

wherein the optical system is constructed so that light beams simultaneously enter the dielectric blocks of at least two measuring units supported by the supporting body; and wherein the photodetection means comprises at least two photodetectors provided so that they correspond in number to the light beams which enter the dielectric blocks.

Examples of a measuring apparatus as described above are: a surface plasmon measuring apparatus, which utilizes a metal film as the aforementioned thin film layer; a leaky mode measuring apparatus, which utilizes a layer constituted of a cladding layer formed on a surface of a dielectric block and an optical waveguide layer formed atop the cladding layer as the aforementioned thin film layer; etc.

The measuring apparatus of the present invention can employ various methods of analyzing a sample by measuring the intensity of the light beam totally reflected at the aforementioned interface with photodetection means. For example, a sample can be analyzed by causing a light beam to strike the aforementioned interface at various angles of incidence so that a total internal reflection condition is satisfied at the interface, then measuring the intensity of the light beam totally reflected at the interface at each of the positions corresponding to the incidence angles, and detecting the position (angle) of a dark line occurring due to attenuated total reflection (ATR).

In addition, a sample can be analyzed by causing a light beam with a plurality of wavelengths to strike the aforementioned interface at an angle of incidence so that a total internal reflection condition is satisfied at the interface, then measuring the intensity of the light beam of each wavelength totally reflected at the interface, and detecting the degree of ATR for each wavelength (see, D. V. Noort, K. johansen, C.-F. Mandenius, Porous Gold in Surface Plasmon Resonance Measurement, EUROSENSORS XIII, 1999, PP. 585–588).

Furthermore, a sample can be analyzed by causing a light beam to strike the aforementioned interface at an angle of incidence so that a total internal reflection condition is satisfied at the interface, then splitting the light beam into two light beams before the light beam strikes the interface, causing one of the two light beam to interfere with the other totally reflected at the interface, and detecting the intensity of the light beam after the interference (see P. I. Nikitin, A. N. Grigorenko, A. A. Beloglazov, M. V. Valeiko, A. I. Savchuk, O. A. Savchuk, Surface Plasmon Resonance Interferometry for Micro-Arrary Biosensing, EUROSENSORS XIII, 1999, PP. 235–238).

In the aforementioned measuring apparatuses of the present invention, the optical system may be constructed so that light beams simultaneously enter the dielectric blocks of all the measuring units supported by the supporting body.

In the aforementioned measuring apparatuses of the present invention, the light source may comprise one or a plurality of light sources, and the optical system may be constructed so that a single light beam emitted from each of the one or the plurality of light sources branches into a plurality of light beams, and that the plurality of light beams respectively enter the dielectric blocks. For example, in the case where the number of measuring units that a light beam enters is 8, a single light beam emitted from a single light source can be branched into 8 light beams. In addition, a single light emitted from each of two light sources can be branched into 4 light beams so that 8 light beams are obtained in total.

In the aforementioned measuring apparatuses of the present invention, the light source may comprise one or plurality of light sources, and the optical system may be constructed so that a light beam emitted from each of the one or plurality of light sources is flattened, and that the flattened light beam enters the dielectric blocks. For instance, in the case where the number of measuring units that a light beam enters is 8, a single light beam emitted from a single light source can be flattened so that it enters 8 measuring units at the same time. In addition, a light beam emitted from each of two light beams can be flattened so that it enters the measuring units at the same time.

In the aforementioned measuring apparatuses of the present invention, the light source may comprise a number of light sources that corresponds to the number of the measuring units, and the optical system may be constructed so that light beams emitted from each of the light sources respectively enter the dielectric blocks.

The aforementioned measuring apparatuses of the present invention may further comprise drive means for relatively moving the supporting body and the optical system and photodetection means so that each of the measuring units is held selectively at either a measuring position at which the light beam enters the dielectric body or a standby position at which no light beam enters the dielectric body. Note that instead of a single standby position, a plurality of standby positions may be provided.

In the case of employing the aforementioned drive means, the supporting body linearly may arrange a plurality of measuring units in a row and support them, and the drive means may relatively move the supporting body and the optical system and photodetection means linearly in a direction where the plurality of measuring units are arranged.

Alternatively, in the case of employing the aforementioned drive means, the supporting body may arrange a plurality of measuring units on a circle and support them, and the drive means may relatively move the supporting body and the optical system and photodetection means linearly in a direction where the plurality of measuring units are arranged.

In the case of employing the aforementioned drive means, the optical system and the photodetection means may be held in a stationary state, and the drive means may move the supporting body. Conversely, the supporting body may be held in a stationary state, and the drive means may move the optical system and the photodetection means.

Note that in the case of employing the aforementioned drive means, the number of measuring units do not always coincide with the number of light beams emitted from the aforementioned optical system. For example, in the case where the number of measuring units that a light beam enters is 8, the optical system can be constructed so that 4 light beams are emitted. First, the 4 light beams are irradiated to 4 measuring units. Then, the remaining 4 measuring units are moved to the aforementioned measuring position by the drive means. Next, the 4 light beams are irradiated to the remaining 4 measuring units.

The measuring apparatus of the present invention may further comprise measuring-unit supply means for removing the measuring unit held in the standby position from the supporting body, and returning the removed measuring unit to the supporting body again.

In the measuring apparatus of the present invention, the supporting body may arrange and support a plurality of measuring units in a first direction so that the light beam enters the measuring units at the same time, and may also arrange and support a plurality of measuring units in a second direction perpendicular to the first direction. In this case, the measuring apparatus may further comprise measuring-unit feed means for relatively moving the supporting body and the optical system and photodetection means in the second direction, and moving the plurality of measuring units arranged in the second direction, to a position so that the light beam serially enters the measuring units.

In the aforementioned measuring apparatuses, the dielectric blocks and the supporting body may be integrally formed.

In the present invention, preservation means for preserving the measuring unit under temperature control may be provided at the standby position. In addition, state detection means for detecting a state of the measuring unit may be provided at the standby position.

After a sample is poured into the measuring unit, drift occurs for a while in a signal detected by the measuring apparatus. The major cause of a drift in the detected signal is that it takes time for the poured sample to conform to the measuring unit, and meanwhile a fluctuation in temperature, etc., occurs in the measuring unit. The aforementioned state detection means is used to detect the above-mentioned transient response state. For example, the temperature of the measuring unit (sample) may be detected with a temperature sensor, or a change in the refractive index of the sample may be detected with a sensor utilizing an evanescent wave.

In addition, the measuring apparatus according to the present invention may be equipped with timing instruction means for instructing timing at which a detecting operation is performed by the photodetection means.

Furthermore, in the measuring apparatus according to the present invention, the optical incidence system may comprise a plurality of optical incidence systems, the photodetection means may comprise a plurality of photodetection means, and the plurality of photodetection means may correspond in number to the plurality of optical incidence means. That is, it is desirable that multiple measurements are capable of being performed simultaneously by the plurality of optical incidence systems and their corresponding photodetection means.

In accordance with the present invention, there is provided a first measuring chip for use in a measuring apparatus constructed of a light source for emitting a light beam, an optical incidence system for making the light beam enter the dielectric block at an angle of incidence so that a total internal reflection condition is satisfied at an interface between the dielectric block and the thin film layer, and photodetection means for measuring the intensity of the light beam totally reflected at the interface. The first measuring chip comprises a dielectric block, and a thin film layer, formed on a surface of the dielectric block, which is contacted with a sample. In the first measuring chip, a plurality of measuring units, which comprise the aforementioned dielectric block and the aforementioned thin film, are arranged in a row and integrated.

Examples of a measuring chip as described above are: those for use in a surface plasmon measuring apparatus, which utilize a metal film as the aforementioned thin film layer; those for use in a leaky mode measuring apparatus, which utilize a layer constituted of a cladding layer formed on a surface of a dielectric block and an optical waveguide layer formed atop the cladding layer as the aforementioned thin film layer; etc.

In the aforementioned measuring chips of the present invention, the dielectric blocks of the integrated measuring units may be discretely formed, and the discrete dielectric blocks may be connected together and integrated by a connecting member. Alternatively, the dielectric blocks of the integrated measuring units may be formed from a single member.

In the aforementioned measuring chips of the present invention, there is provided a sample holding mechanism for holding the sample on the thin film layer.

In addition, the dielectric block may be formed from either glass or transparent resin. In the case of employing transparent resin, it is desirable that the sample holding mechanism and the dielectric bodies be integrally formed.

In the aforementioned measuring chips of the present invention, a sensing substance that bonds with a specific substance in the sample may be fixed on the thin film layer.

In the aforementioned measuring apparatuses, as described above, a plurality of measuring units, which are equipped with a dielectric block, a thin film layer (which is a metal film in the case of utilizing surface plasmon resonance, or a cladding layer and an optical waveguide layer in the case of utilizing the excitation of a waveguide mode), and a sample holding mechanism, are supported by the supporting body. In addition, light beams are simultaneously irradiated from the optical system to at least two dielectric bodies of the measuring units, and the number of the photodetectors corresponds to the number of light beams that enter the dielectric bodies. Therefore, at least two measuring units can be measured at the same time. Thus, the present invention is capable of measuring a great number of samples in a short time.

Particularly, in the case where the aforementioned optical system is constructed so that a single light beam emitted from the light source is branched into a plurality of light beams or flattened and that the light beams (or a flattened light beam) simultaneously enter the dielectric bodies of all the measuring units supported by the aforementioned supporting body, the measuring units can be simultaneously measured. Thus, it becomes possible to measure a great number of measuring units in a shorter time.

In the case where a sensing substance that interacts with a specific component in a sample is placed on the surface of the film layer and the sample is held on the surface of the sensing substance, the interaction changes the state of surface plasmon resonance or the excited state of a waveguide mode, i.e., the state of attenuated total reflection (ATR). Based on this change, the specific reaction between the specific component in the sample and the sensing substance can be detected.

In the case of employing the aforementioned drive means for relatively moving the aforementioned supporting body and the aforementioned optical system and photodetection means to selectively hold the measuring units at either a measuring position where the light beam enters the dielectric body or a standby position where no light beam enters the dielectric body, the supply or removal of the measuring units with respect to the supporting body, dropping of samples, etc., can be performed at the standby position. Thus, the efficiency of the measuring operation can be enhanced.

In the case of employing the aforementioned measuring-unit supply means for removing the measuring unit held in the standby position from the supporting body and returning the removed measuring unit to the supporting body again, the efficiency of the measuring operation can be enhanced when measuring a single sample a plurality of times, like the aforementioned random screening. That is, if a sample in the measuring units being supported by the supporting body is measured once, then the measuring units are moved to the standby position and removed from the supporting body. Then, another plurality of measuring units are supported by the supporting body and are measured. Next, the current measuring units are moved to the standby position and removed from the supporting body. Next, the previous measuring units are again supported by the supporting body and are again measured. In this manner, the intervals between a plurality of measurements on one sample can be effectively utilized to measure another sample. Thus, a great number of samples can be measured in a shorter time.

In the measuring apparatus of the present invention, the supporting body arranges and supports a plurality of measuring units in a first direction so that the light beam enters the measuring units at the same time, and also arranges and supports a plurality of measuring units in a second direction perpendicular to the first direction. Furthermore, the measuring apparatus is provided with measuring-unit feed means for relatively moving the supporting body and the optical system and photodetection means in the second direction, and moving the plurality of measuring units arranged in the second direction, to a position so that the light beam serially enters the measuring units. In this case, the efficiency of the measuring operation can be further enhanced. That is, if the measuring units arranged in the first direction are measured and then the supporting body and the optical system and photodetection means are relatively moved in the second direction, another plurality of measuring units arranged in the first direction can be immediately measured. Thus, it becomes possible to measure a great number of measuring units within an extremely short time.

In the case where the dielectric bodies and the supporting body are integrally formed, the operation of supporting the dielectric bodies on the supporting body one by one becomes unnecessary and therefore the efficiency of the measuring operation can be further enhanced.

On the other hand, according to the measuring chip of the present invention, a plurality of measuring units, which comprise a dielectric block and a thin film layer (which is a metal film in the case of utilizing surface plasmon resonance, or a cladding layer and an optical waveguide layer in the case of utilizing the excitation of a waveguide mode), are arranged in a row and integrated. Therefore, the integrated measuring chip becomes greater in size than a single measuring chip consisting of a single measuring unit. Because of this, the positional accuracy in the surface plasmon resonance measuring apparatus can be easily obtained, and the integrated measuring chip is easy to handle. If the positional accuracy of the measuring chip in the measuring apparatus is obtained, the accuracy of measurement is enhanced. In addition, if the measuring chip is easy to handle, the efficiency of the measuring operation is enhanced.

In addition, the measuring chip according to the present invention is equipped with a plurality of measuring units. Therefore, with the supply or removal of a single measuring chip, a plurality of measuring units can be supplied to or removed from the measuring apparatus. This is also able to contribute to an enhancement in the efficiency of the measuring operation.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
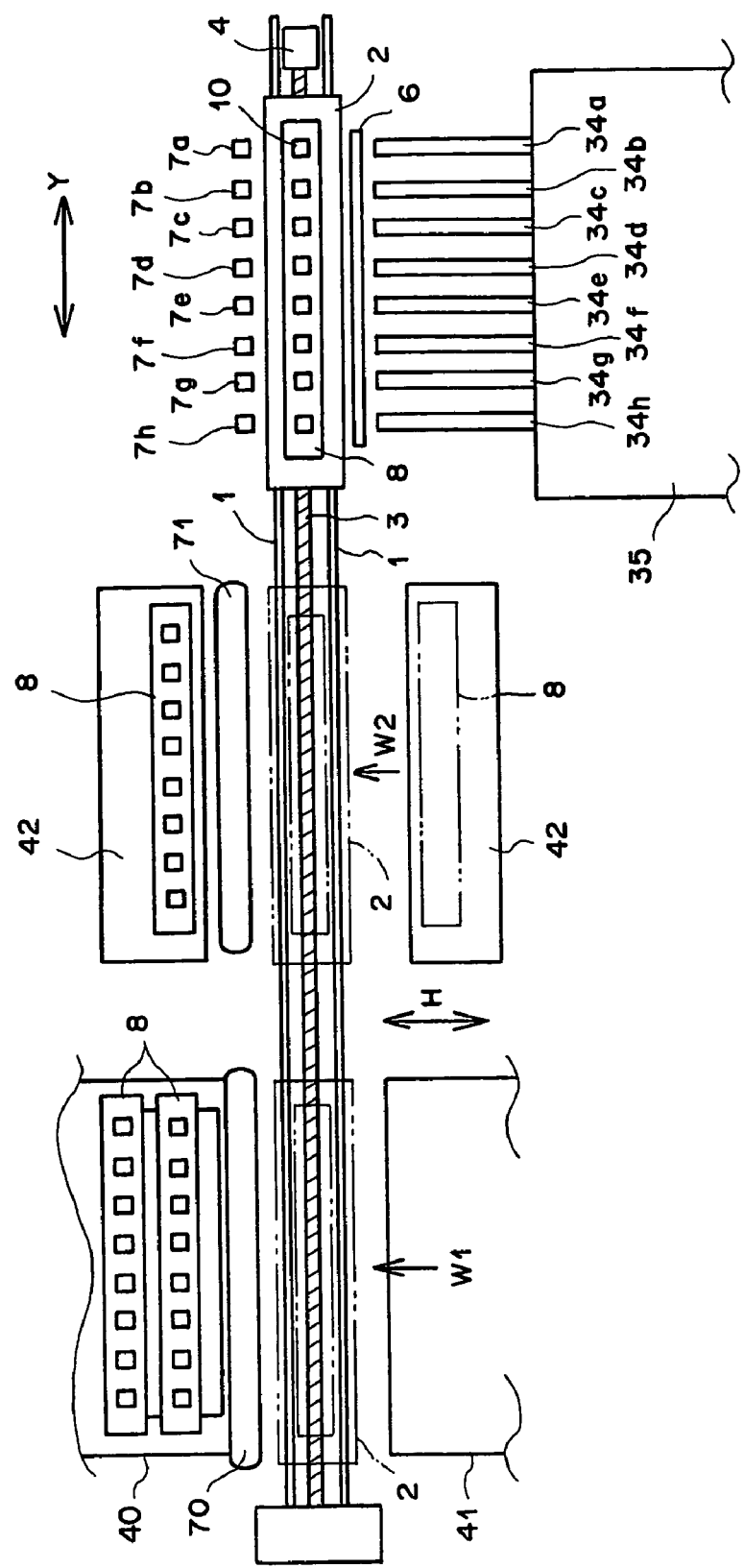
FIG. 1 is a plan view showing a surface plasmon resonance measuring apparatus according to a first embodiment of the present invention.
Figure 2:
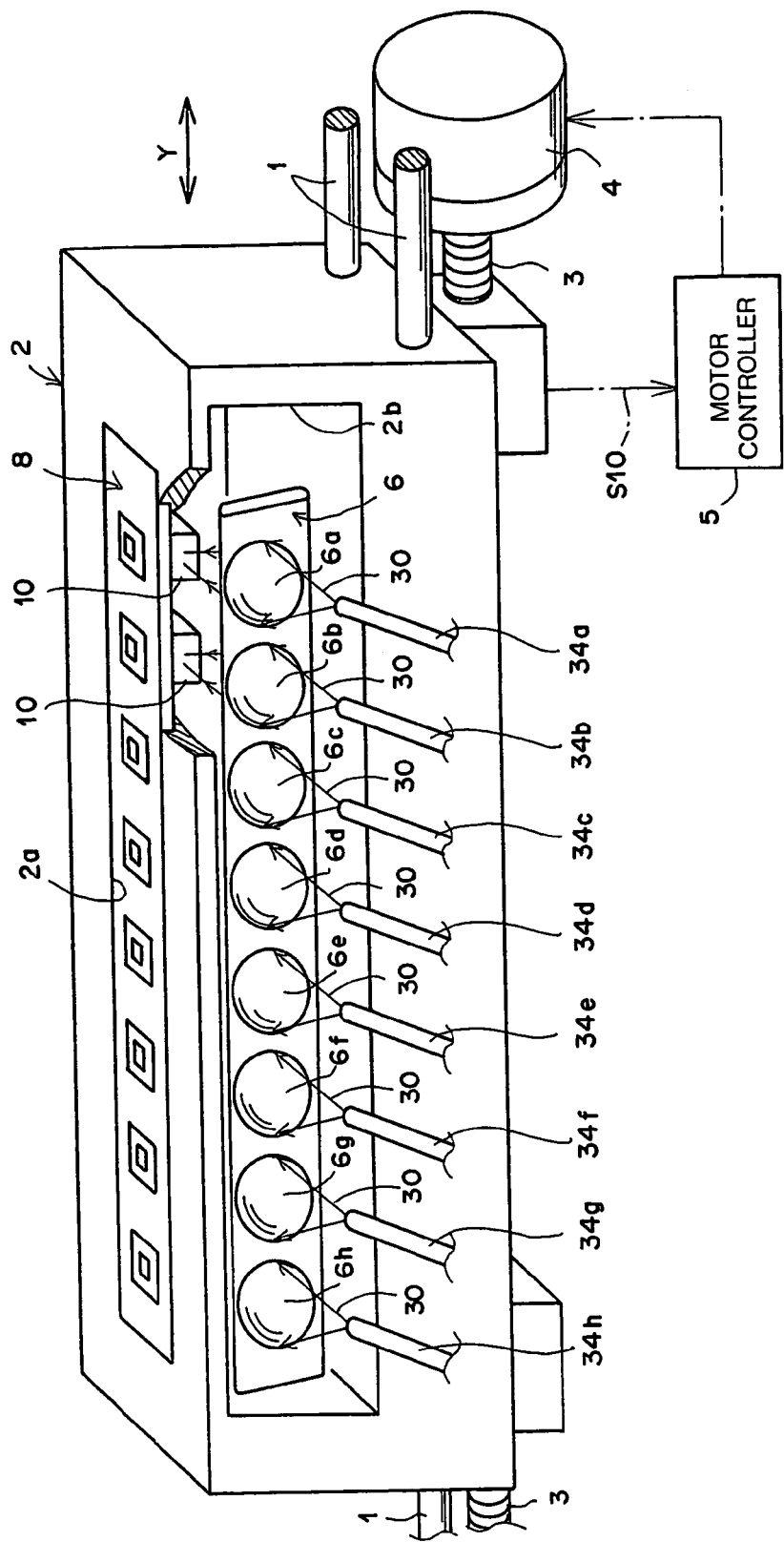
FIG. 2 is a perspective view showing the essential parts of the surface plasmon resonance measuring apparatus shown in FIG. 1.
Figure 3:
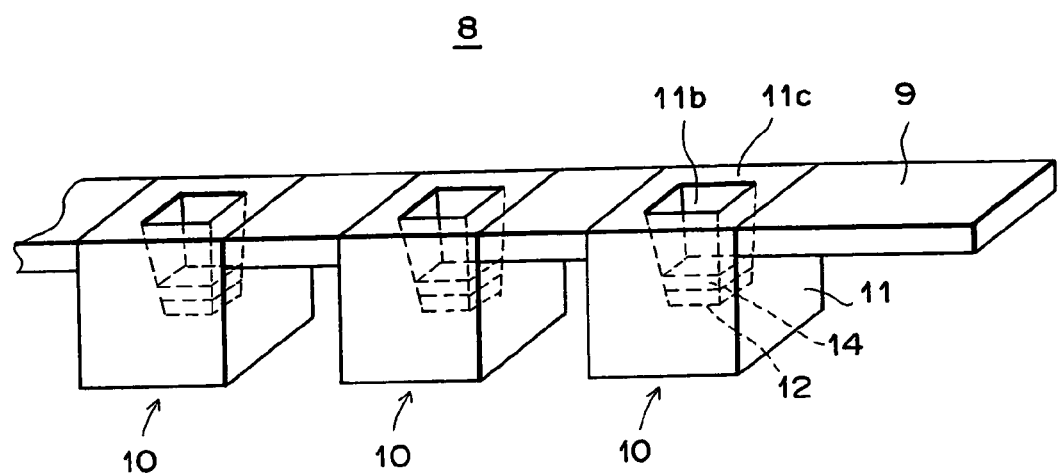
FIG. 3 is a perspective view showing a measuring-unit connecting body employed in the surface plasmon resonance measuring apparatus shown in FIG. 1.

Embodiments of the present invention will hereinafter be described in detail with reference to the drawings. FIG. 1 shows a surface plasmon resonance measuring apparatus according to a first embodiment of the present invention. FIG. 2 shows the essential parts of the surface plasmon resonance measuring apparatus. FIG. 3 shows a measuring-unit connecting body, which is a measuring chip, employed in the surface plasmon resonance measuring apparatus.

As shown in FIGS. 1 and 2, the surface plasmon resonance measuring apparatus has a slide block 2 as a supporting body for supporting measuring units 10 to be described later. The slide block 2 slidably engages with two parallel guide rods 1, 1 so that it is linearly movable in the direction of arrow Y (i.e., the longitudinal direction of the measuring-unit connecting body 8 to be described later) along them. This slide block 2 meshes with a fine screw 3 disposed in parallel to the guide rods 1, 1. The screw 3 is rotated in positive and reverse directions by a pulse motor 4. The screw 3 and the pulse motor 4 constitute supporting-body drive means.

The pulse motor 4 is controlled by a motor controller 5. That is, the motor controller 5 is provided within the slide block 2; receives a signal S10 output from a linear encoder (not shown) for detecting the position of the slide block 2 with respect to the longitudinal direction of the guide rods 1, 1; and controls the pulse motor 4, based on the signal S10.

The surface plasmon resonance measuring apparatus of the first embodiment employs a stick-shaped measuring-unit connecting body 8 in which eight measuring units 10 are connected and fixed as an example. The eight measuring units 10 are held in a row in the slide block 2. FIG. 3 shows the detailed structure of the measuring-unit connecting body 8. As shown in the figure, the measuring-unit connecting body 8 has a connecting member 9 by which the eight measuring units 10 are connected.

The measuring unit 10 has a transparent dielectric block 11 and a metal film 12, as shown in FIG. 3. The dielectric block 11 is formed, for example, into a generally rectangular parallelepiped. The metal film 12 is made of metal such as gold, silver, copper, aluminum, etc., and is formed on the bottom of a hole 11b provided in the dielectric body 11. The hole 11b of the dielectric body 11 constitutes a sample container 11c, which is used for holding a sample (e.g., a liquid sample) on the metal film 12, that is, in the hole 11b.

The dielectric body 11 is molded by injection molding of transparent resin, etc., and constitutes an exchangeable measuring unit with respect to the slide block 2. In the first embodiment, a sensing substance 14 is fixed on the metal film 12, as described in detail later.

Figure 4:
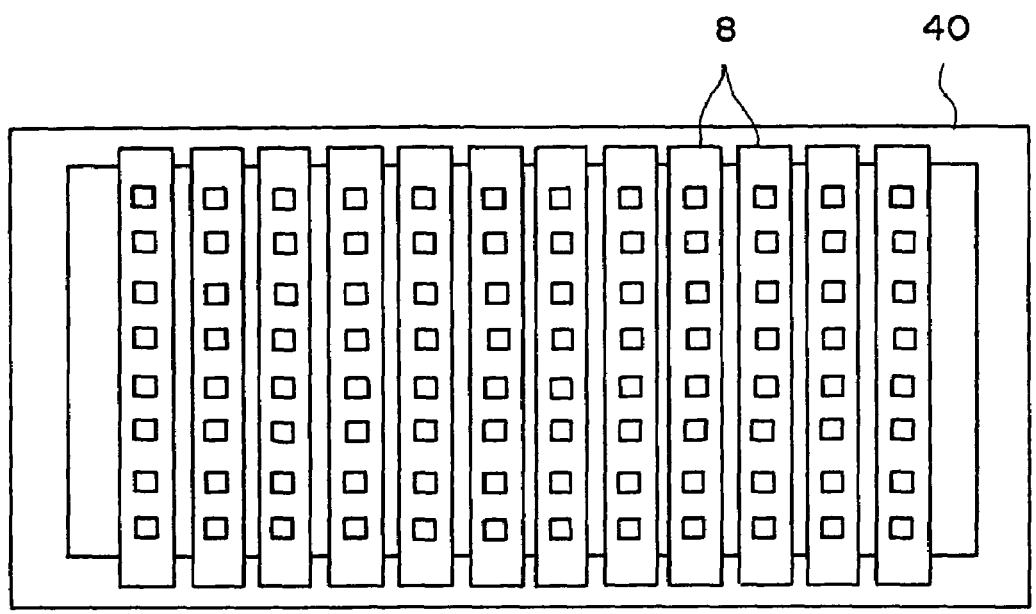
FIG. 4 is a plan view showing a means for housing the measuring-unit connecting body shown in FIG. 3.

As shown in FIG. 4, a plurality of measuring-unit connecting bodies 8 are placed on a plate 40. In the first embodiment, twelve measuring-unit connecting bodies 8 are placed on the plate 40. In this state, the plate 40 is carried and handled. That is, 96 measuring units 10 can be carried and handled by a single plate 40.

Figure 5:
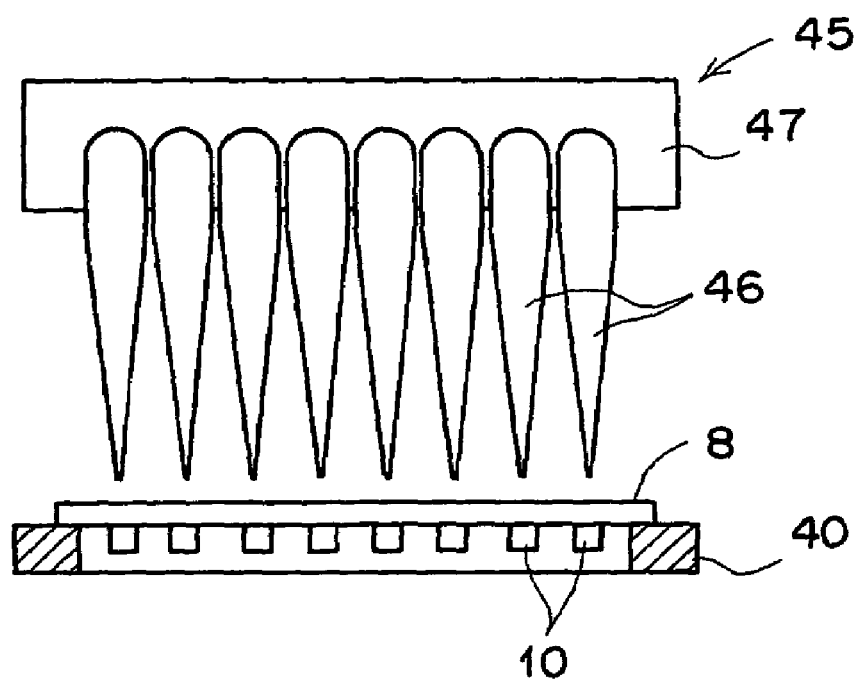
FIG. 5 is a front view showing a means for supplying samples to the measuring-unit connecting body of FIG. 3.

In the case where a plurality of measuring units 10 are thus handled as the measuring-unit connecting body 8, it is desirable to use a distributor 45 such as that shown in FIG. 5, as a means for supplying liquid samples to the measuring units 10. This distributor 45 has a number of distributor nozzles 46 that corresponds to the number of measuring units 10. The distributor nozzles 46 have the same pitch as the pitch between the measuring units 10 and are supported by a supporting member 47. Thus, liquid samples can be distributed to the plurality of measuring units 10 of the single measuring-unit connecting body 8, so the efficiency of the sample supplying operation can be enhanced.

Figure 6:
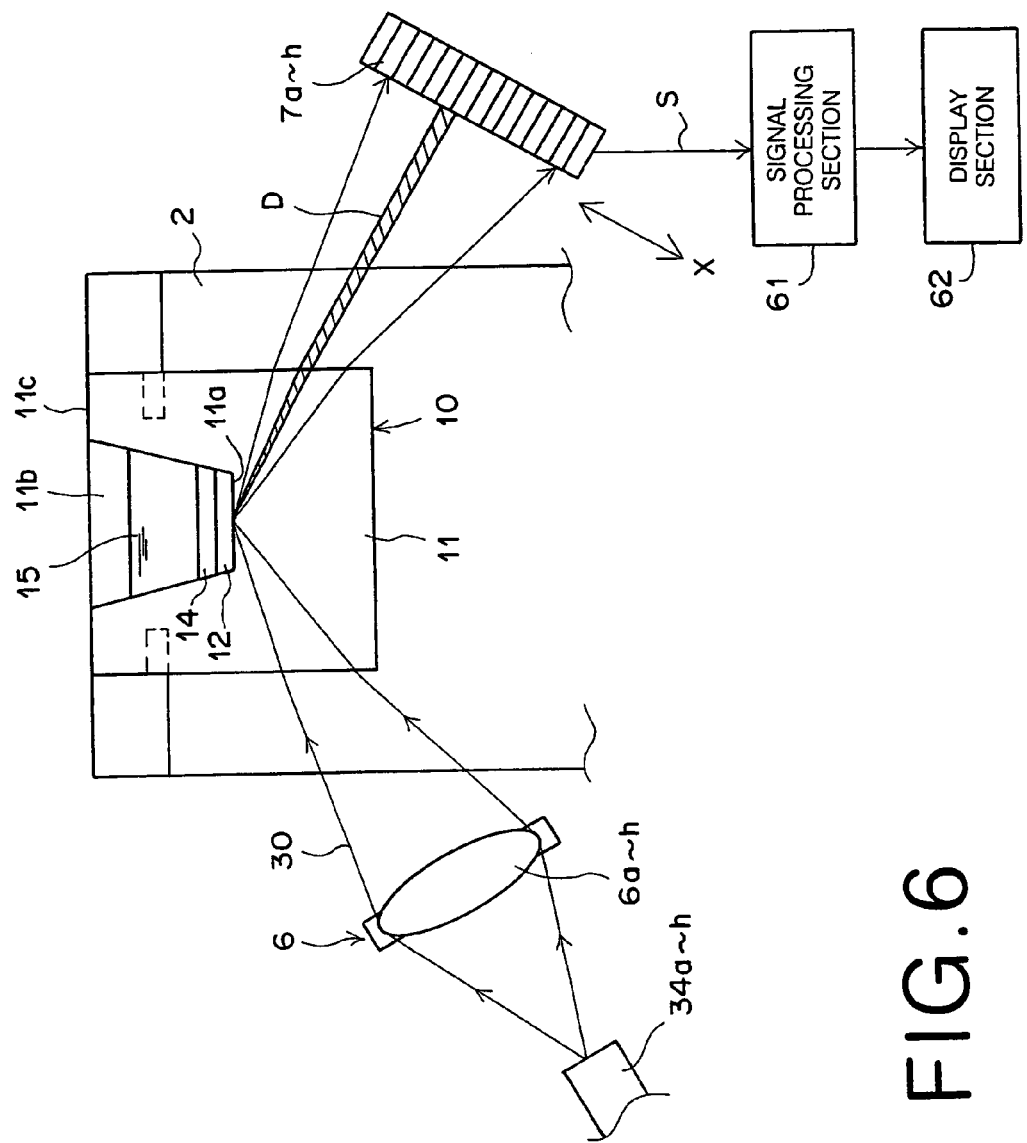
FIG. 6 is a side view showing the essential parts of the surface plasmon resonance measuring apparatus shown in FIG. 1.

As shown in FIGS. 1, 2 and 6, a microlens array 6 and eight photodetectors 7a to 7h are disposed above the guide rods 1, 1 so that the slide block 2 is interposed therebetween. The microlens array 6 has eight convex lenses 6a to 6h that are respectively aligned with the eight measuring units 10 held in the slide block 2. The photodetectors 7a to 7h are similarly disposed so that they are aligned with the eight measuring units 10 held in the slide block 2. Each of the photodetectors 7a to 7h is constructed of a line sensor in which a great number of light-receiving elements are arranged in a row. The light-receiving elements are arranged in the direction of arrow X shown in FIG. 6.

Figure 7:
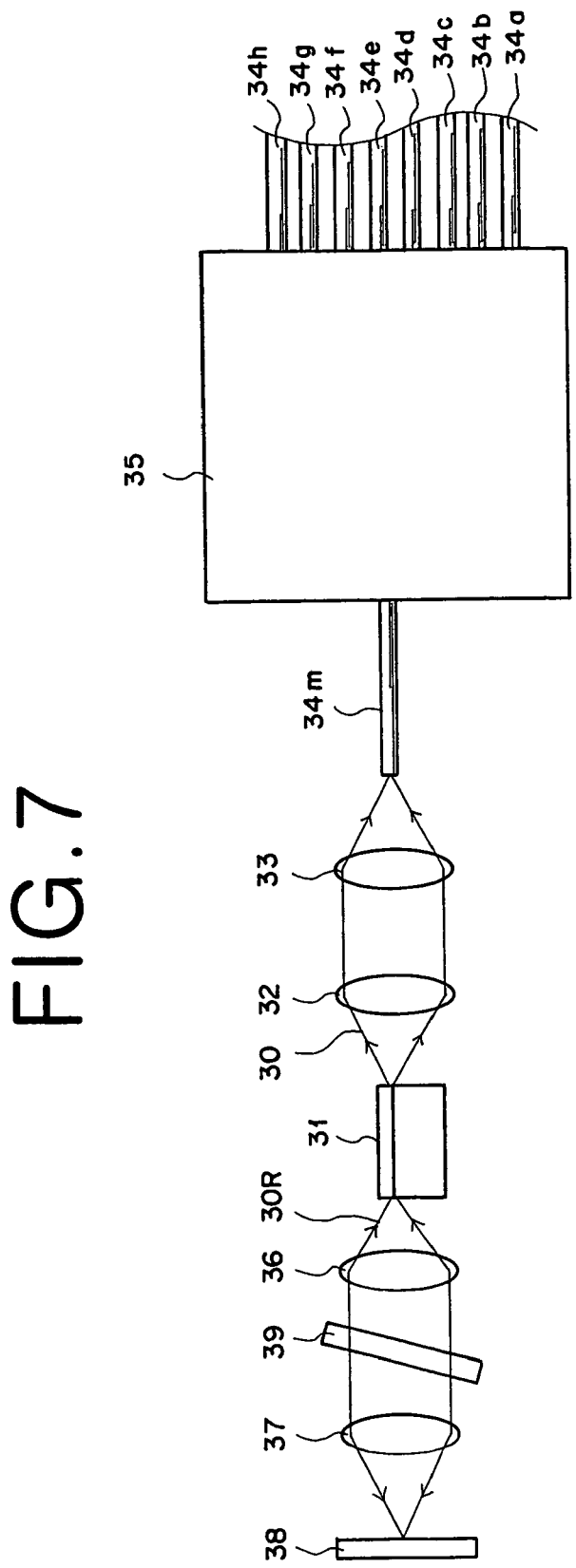
FIG. 7 is a plan view showing the optical system of the surface plasmon resonance measuring apparatus shown in FIG. 1.

Optical fibers 34a to 34h are disposed on the optical axes of the convex lenses 6a to 6h of the microlens array 6 so that the divergent optical beams 30 emitted therefrom strike the convex lenses 6a to 6h. FIG. 7 shows an optical system including the optical fibers 34a to 34h, and a light source. A description will hereinafter be given of the construction shown in FIG. 7.

The light source of the first embodiment employs, for example, a semiconductor laser 31 for emiting a light beam (laser beam) 30 whose wavelengths are in the infrared region. The light beam 30 emitted divergently by this semiconductor laser 31 is collimated by a collimator lens 32. Then, the collimated light beam 30 is condensed by a condenser lens 33 and enters an optical fiber 34m. The optical fiber 34m is connected to an optical coupler unit 35. In the optical coupler unit 35, an input light beam is branched at a branching ratio of 50:50 through three stages. That is, the input light beam is branched into 2 beams at the first stage, 4 beams at the second stage, and 8 beams at the third stage. Thus, the light beam 30 input to the optical fiber 34m is branched into 8 light beams having an equal light quantity. The 8 light beams are guided to the optical fibers 34a to 34h, respectively.

Note that the faces of the optical components on the downstream side of the semiconductor laser 31 through which light is transmitted are provided with antireflection (AR) coatings, including the end faces of the optical fibers 34a to 34h and 34m. These AR coatings eliminate the problem of noise that will occur when the light reflected at these faces return to the semiconductor laser 31.

In addition, the front and rear end faces of the semiconductor laser 31 are provided with low-reflection (LR) coatings, respectively. Because of this, a light beam 30R is emitted backward from the semiconductor laser 31. The backward light beam 30R is collimated by a collimator lens 36 and condensed by a condenser lens 37. At a position where the backward light beam R condensed by the condenser lens 37 is converged, there is disposed a mirror 38. The backward light beam 30R is reflected by the mirror 38 and is fed back to the semiconductor laser 31. At this time, the backward light beam 30R is transmitted through a narrow-band pass filter 39 inserted between the collimator lens 36 and the condenser lens 37, and the wavelength of the backward light beam 30R is selected. Thus, the backward light beam 30R with the selected wavelength is fed back to the semiconductor laser 31. Hence, the emission wavelength of the semiconductor laser 31 is locked to the selected wavelength and stabilized.

A description will hereinafter be made of how samples are analyzed by the surface plasmon resonance measuring apparatus described above. When analyzing samples, the slide block 2 is first moved to a first standby position shown by arrow W1 in FIG. 2, and then one measuring-unit connecting body 8 is fitted from the plate 40 (see FIG. 4) into the measuring-unit holding portion 2a of the slide block 2. Note that a liquid sample 15 to be measured (see FIG. 6) has previously been held in the hole 10b of each measuring unit 10 of the measuring-unit connecting body 8. The fitting of the measuring-unit connecting body 8 into the slide block 2 is performed by a measuring-unit supply mechanism 70.

The measuring-unit supply mechanism 70 is freely movable in the horizontal direction perpendicular to the guide rods 1,1 (i.e., the direction of arrow H shown in FIG. 1) and the vertical direction (i.e., the direction perpendicular to the surface of the drawing sheet in FIG. 1), and has suction cups for holding the right and left end portions of the measuring-unit connecting body 8 at the right and left end portions thereof by suction. The measuring-unit supply mechanism 70 moves to a position above a target measuring-unit connecting body 8 on the plate 40 and then moves downward, then holds the measuring-unit connecting body 8 and moves upward, further moves to a position right above the slide block 2 being held at the first standby position, then moves downward and fits the measuring-unit connecting body 8 into the measuring-unit holding portion 2a of the slide block 2, and releases the holding of the measuring-unit connecting body 8 and moves upward. In this manner, the measuring-unit connecting body 8 is fitted in the slide block 2.

After the measuring-unit connecting body 8 is fitted in the slide block 2 in the aforementioned manner, the pulse motor 4 is driven by the motor controller 5 so that the slide block 2 is moved to a measuring position indicated by a solid line. At this time, the slide block 2 is moved to the measuring position in the longitudinal direction of the measuring-unit connecting body 8. Therefore, the tilt of the measuring-unit connecting body 8 that is caused during movement can be reduced, and the influence of the tilt of the measuring-unit connecting body 8 on positional accuracy can be reduced.

A measurement of surface plasmon resonance that is made at the measuring position will hereinafter be described with reference to FIG. 6. Although a description will be given of one of the eight measuring units 10 of the measuring-unit connecting body 8 which is aligned with the optical fiber 34a and photodetector 7a, the remaining units 10 can be measured in the same manner.

When measuring surface plasmon resonance, the semiconductor laser 31 shown in FIG. 7 is driven. As shown in FIG. 6, the light beam 30 is emitted divergently from the end face of the optical fiber 34a. The emitted light beam 30 is condensed by the convex lens 6a of the microlens array 6. The condensed light beam 30 enters the dielectric block 11 and then strikes the interface 11a between the dielectric block 11 and the metal film 12 at various angles of incidence so that a total internal reflection condition for the light beam 30 is satisfied at the interface 11a and that surface plasmon resonance occurs.

Note that the p-polarized component of the light beam 30 is caused to strike the interface 11a. To make the p-polarized component strike the interface 11a, the semiconductor laser 31 is disposed so that the polarization direction thereof becomes a predetermined direction, and the optical fibers 34m and 34a to 34h employ polarization-preserving fibers. In this manner, the polarization direction of the light beam 30 emitted from each optical fiber is controlled. The polarization direction of the light beam 30 may be controlled with a wavelength plate or polarizing plate.

The light beam 30 incident on the interface 11a is totally reflected at the interface 11a, and the totally reflected light beam 30 is detected by the photodetector 7a. As described above, the light beam 30 strikes the interface 11a at various angles of incidence, so the totally reflected light beam 30 contains components reflected at various angles.

Figure 8:
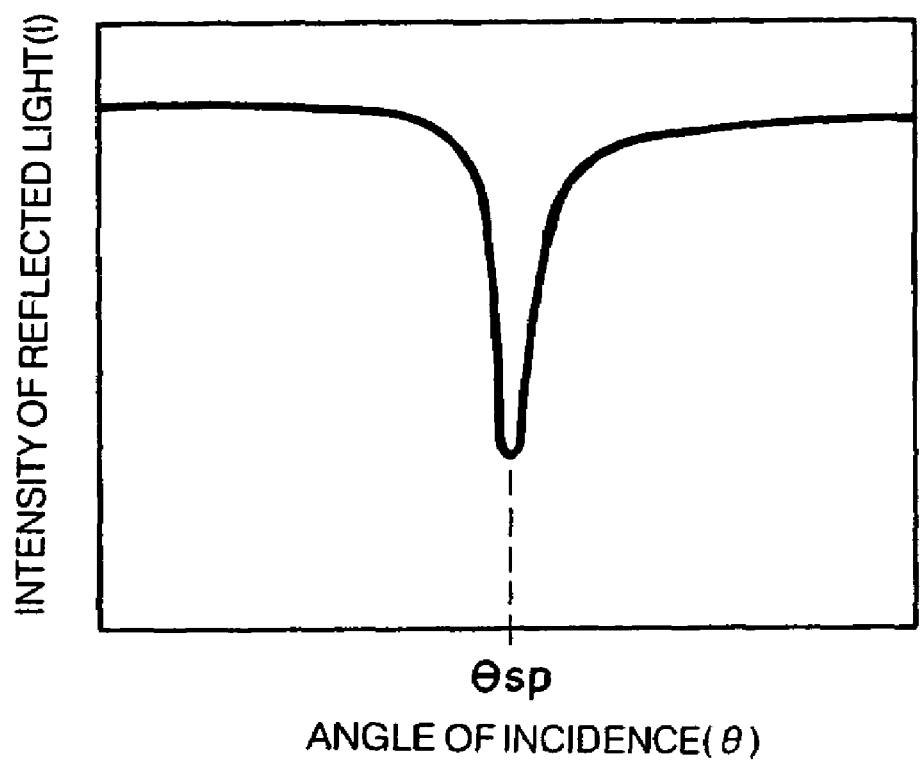
FIG. 8 is a graph showing the relationship between the incidence angle of a light beam in the surface plasmon resonance measuring apparatus and the intensity of the reflected light.

If the light beam 30 is totally reflected as described above, an evanescent wave propagates in the metal film 12 through the interface 11a. When the light beam 30 strikes the interface 11a at a specific incidence angle $\theta_{sp}$, the intensity I of the reflected light drops sharply, because the evanescent light resonates with surface plasmon excited on the surface of the metal film 12. This sharp intensity drop is observed as a dark line D in the totally reflected light beam 30. The relationship between the specific incidence angle $\theta_{sp}$ and the intensity I of the reflected light is shown in FIG. 8.

The quantity of light detected by each light-receiving element is examined from a light-quantity detection signal S output from the photodetector 7a. Based on the position of the light-receiving element detecting a dark line, the aforementioned specific incidence angle $\theta_{sp}$ (at which ATR occurs) is found. According to a previously calculated curve representing the relationship between the intensity I and the incidence angle $\theta$, a specific substance in the sample 15 is quantitatively analyzed. A signal processing section 61 is used for quantitatively analyzing a specific substance in the sample 15 according to the aforementioned principle, and the result of analysis is displayed on a display section 62.

As shown in FIG. 2, the slide block 2 has an opening 2b extending in the longitudinal direction thereof so that the light beams 30 can be irradiated to the measuring units 10 without being intercepted by the slide block 2. In addition, the light beam 30 totally reflected at the interface 11a between the dielectric block 11 and the metal film 12 can be detected by each of the photodetectors 7a to 7h without being intercepted by the slide block 2.

The sensing substance 14 fixed on the surface of the metal film 12 bonds with a specific substance in the sample 15. As an example of combination of the specific substance and the sensing substance 14, there are an antigen and an antibody. In that case, an antigen-antibody reaction can be detected based on the specific incidence angle $\theta_{sp}$ at which ATR occurs. In this case, the refractive index of the sensing substance 14 varies according to the bond between the specific substance and the sensing substance 14, and the characteristic curve of FIG. 8 is horizontally shifted. Therefore, the antigen-antibody reaction can be detected based on the specific incidence angle $\theta_{sp}$. In this case, both the sample 15 and the sensing substance are samples to be analyzed.

The measuring operation described above is likewise performed on the remaining seven measuring units 10 in parallel with the aforementioned one measuring unit 10. That is, the samples held in the eight measuring units 10 are measured at the same time. Note that the irradiation of the light beam 30 and detection of the specific incidence angle $\theta_{sp}$ with respect to the eight measuring units 10 do not always need to be performed in a strictly simultaneous manner. The start times or end times may be slightly different from one another.

Thus, according to the first embodiment, it becomes possible to measure a great number of samples in a short time, because the measurements of the samples 15 of the eight measuring units can be performed simultaneously or at nearly the same time.

Note that the signal processing section 16 may be provided for each of the eight photodetectors 7a to 7h, or one signal processing section may be shared by the eight photodetectors 7a to 7h. In this case, the light-quantity detection signals S output from the photodetectors 7a to 7h are serially processed.

In the case of measuring one sample 15 only once, the measurement is completed in the operation described above. In this case, the pulse motor 4 is rotated in the direction opposite to the aforementioned case, and the slide block 2 (i.e., measuring units 10) is returned to a first standby position indicated by arrow W1 in FIG. 1. The measuring unit 8 is removed from the slide block 2 by the measuring-unit supply mechanism 70 and discharged, for example, onto a discharge plate 41.

Next, another measuring-unit connecting body 8 on the plate 40 is similarly set in the measuring-unit holding portion 2a of the slide block 2 by the measuring-unit supply mechanism 70, and the samples 15 held in the 8 measuring units 10 of the measuring-unit connecting body 8 are measured in the same manner as in the aforementioned case.

On the other hand, in the case of measuring one sample 15 a plurality of times, the pulse motor 4 is rotated in the direction opposite to the aforementioned case to move the slide block 2 to a second standby position indicated by arrow W2 in FIG. 1, if the above-mentioned operation is completed. Then, the measuring-unit connecting body 8 is removed from the slide block 2 by a measuring-unit supply mechanism 71 constructed the same as the aforementioned measuring-unit supply mechanism 70. The removed measuring-unit connecting body is placed on either of the mounting tables 42, 42 provided across the guide rods 1, 1.

Next, the pulse motor 4 is again rotated, and the slide block 2 is returned to the first standby position indicated by arrow W1 in FIG. 1. Next, another measuring-unit connecting body 8 is fitted in the measuring-unit holding portion 2a. The samples 15 held in the eight measuring units 10 of the measuring-unit connecting body 8 are also measured in the same manner as in the aforementioned case.

If the measurements of the samples 15 in the measuring units 10 of this second measuring-unit connecting body 8 are completed, the pulse motor 4 is rotated and the slide block 2 is moved to the second standby position. Then, the measuring-unit connecting body 8 is removed from the slide block 2 by the measuring-unit supply mechanism 71 and placed on an empty mounting table of the two mounting tables 42, 42.

Next, the measuring-unit connecting body 8 being placed on the other mounting table 42, that is, the first measuring-unit connecting body 8 is held in the measuring-unit holding portion 2a of the slide block 2 by the measuring-unit supply mechanism 71. The samples 15 held in the 8 measuring units 10 of the measuring-unit connecting body 8 are measured in the same manner as in the previous measurement. When a predetermined time has not elapsed since the first measurement of the first measuring-unit connecting body 8 was completed, the slide block 2 is moved to the measuring position indicated by a solid line in FIG. 1 and stays there for a slight time. Thereafter, the measurement is performed.

If the second measurement of the first measuring-unit connecting body 8 is completed, the pulse motor 4 is rotated and the slide block 2 is moved to the second standby position. Then, the first measuring-unit connecting body 8 is removed from the slide block 2 by the measuring-unit supply mechanism 71 and is placed on an empty mounting table of the two mounting tables 42.

Next, the measuring-unit connecting body 8 being placed on the other mounting table 42, that is, the second measuring-unit connecting body 8 is held in the measuring-unit holding portion 2a of the slide block 2 by the measuring-unit supply mechanism 71. The samples 15 held in the eight measuring units 10 of the measuring-unit connecting body 8 are measured in the same manner as in the previous measurement.

If the second measurement of the second measuring-unit connecting body 8 is completed, the pulse motor 4 is rotated and the slide block 2 is moved to the second standby position. Then, the second measuring-unit connecting body 8 is removed from the slide block 2 by the measuring-unit supply mechanism 71 and is placed on an empty mounting table of the two mounting tables 42.

Thereafter, the same operation is repeated, whereby the measurement of the first measuring-unit connecting body 8 and the measurement of the second measuring-unit connecting body 8 are alternately made. In this manner, a waiting time for the measurement of one of the measuring-unit connecting bodies 8 can be effectively utilized. That is, during the waiting time, the other measuring-unit connecting body 8 can be measured. Thus, the efficiency of the measuring operation is enhanced.

If a predetermined number of measurements on the samples 15 held in the measuring units 10 in one measuring-unit connecting body 8 are completed, then the slide block 2 holding the measuring-unit connecting body 8 is returned to the first standby position. Then, the measuring-unit connecting body 8 is removed from the slide block 2 by the measuring-unit supply mechanism 70 and is discharged onto the discharge plate 41.

Next, a third measuring-unit connecting body 8 on the plate 40 is held in the measuring-unit holding portion 2a of the slide block 2 by the measuring-unit supply mechanism 70. Then, the samples 15 held in the measuring units 10 of the measuring-unit connecting body 8 are measured. In this manner, the remaining measuring-unit connecting bodies 8 being held by the plate 40 can be consecutively measured.

In the first embodiment, as described above, the dielectric block 11 (which has the sample container 11c), the metal film 12, and the sensing substance 14 are integrated into the measuring unit 10. The measuring-unit connecting body 8 with a plurality of measuring units 10 is used as an exchangeable measuring chip with respect to the slide block 2. Therefore, if the current measuring-unit connecting body 8 with samples 15 measured is removed from the slide block 2, and a new measuring-unit connecting body 8 is held in the slide block 2, new samples 15 can be consecutively measured. Thus, it becomes possible to measure a great number of samples in an even shorter time.

Note that it is not always necessary to move the slide block 2 to the second standby position and make the measuring-unit connecting body 8 exchangeable there. However, if done like this, a waiting time for the measurement of one measuring-unit connecting body 8 can be effectively utilized to make a measurement of another measuring-unit connecting body 8, as described before. This is particularly preferable, as the efficiency of the measuring operation is enhanced.

In addition, in the case of having the second standby position, there may be provided a turntable which rotates intermittently by a predetermined angle at a time, instead of providing the aforementioned stationary mounting table 42. In this case, a great number of measuring-unit connecting bodies 8 under measurement can be temporarily placed on the turntable, if the turntable is rotated each time the measuring-unit connecting body 8 is discharged.

Furthermore, there is not always a need to move the measuring-unit connecting body 8 (i.e., measuring units 10) between the standby position and the measuring position by employing the slide block 2, etc. For example, a plurality of measuring units 10 may be supported by a stationary supporting body. In this case, measuring light beams are irradiated to the measuring units 10, respectively. In such a case, the supporting body is necessarily disposed in close proximity to the optical system and the photodetection means. Therefore, in the case of supplying and removing the measuring units 10 by automatic means, the automatic means must be constructed so that it does not interfere with the optical system and the photodetection means.

In addition, in the case of moving the supporting body, the present invention is not to be limited to the linear movement described in the first embodiment. For instance, the supporting body can employ a turntable that rotates intermittently by a predetermined angle at a time. In this case, a plurality of measuring units are supported on a circle with the rotation axis of the turntable as the center, and the measuring units are moved along the circle by rotating the turntable. For example, sixteen measuring units can be supported on the turntable. First, eight measuring units are irradiated at once with light beams. After the measurements of the 8 measuring units, the turntable is rotated through 180 degrees and the remaining eight measuring units are irradiated at once with light beams.

Figure 9:
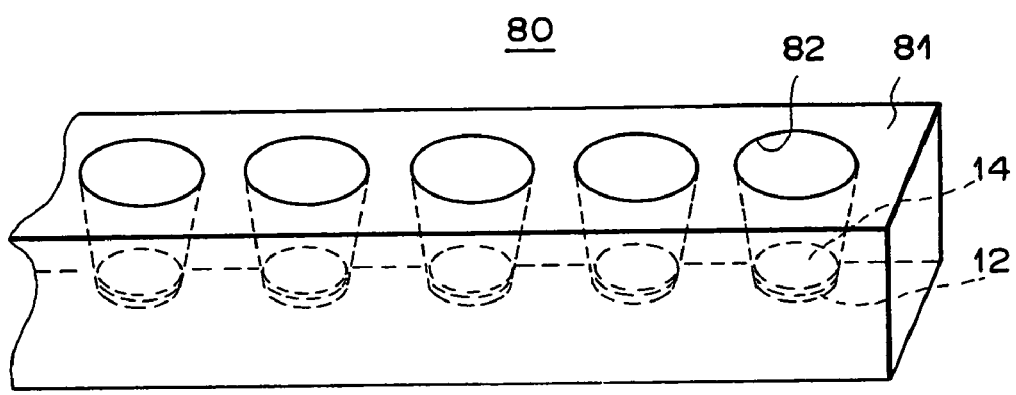
FIG. 9 is a perspective view showing a first modification of the measuring-unit connecting body employed in the surface plasmon resonance measuring apparatus of the first embodiment.
Figure 10:
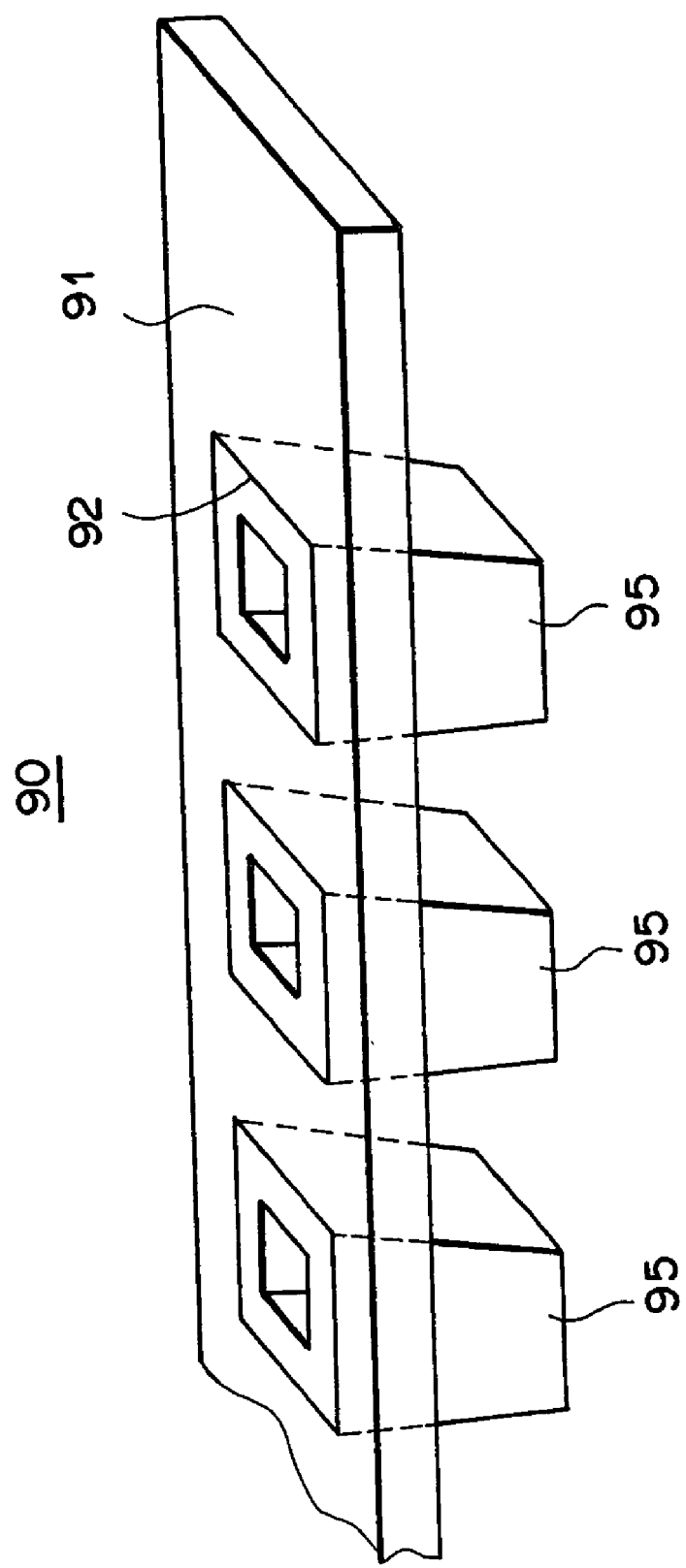
FIG. 10 is a perspective view showing a second modification of the measuring-unit connecting body employed in the surface plasmon resonance measuring apparatus of the first embodiment.

It is also possible employ measuring-unit connecting bodies such as those shown in FIGS. 9 and 10, instead of the measuring-unit connecting body 8 described above. The measuring-unit connecting body 80 is a first modification of the measuring-unit connecting body 8 employed in the first embodiment of the present invention. The measuring-unit connecting body 80 is constructed of a single dielectric bar 81, which is formed from the same material as the dielectric block 11 shown in FIG. 3. The dielectric bar 81 has a plurality of bottomed holes 82, and each hole 82 functions as a sample holding portion. A metal film 12 and a sensing substance 14 are formed on the bottom of each hole 82. Thus, in the measuring-unit connecting body 80, each hole 82 constitutes a measuring unit.

The measuring-unit connecting body 80 constructed as described above is easy to manufacture, compared with the measuring-unit connecting body 8 of FIG. 3 in which a plurality of measuring units 10 are formed one by one and connected together. Thus, a reduction in the manufacturing cost can be realized.

On the other hand, the measuring-unit connecting body 90 shown in FIG. 10 consists of a measuring-unit supporting plate 91, and measuring units 95 fitted in the measuring-unit supporting holes 92 of the supporting plate 91. Each of the measuring units 95 is basically the same as the measuring unit 10 shown in FIG. 3. As shown in FIG. 10, the measuring unit 95 is formed into a truncated pyramid and fitted in the taper-shaped supporting hole 92 so that it cannot be passed through the hole 92. In addition to holding the measuring units 95 by the supporting holes 92, it is desirable that the measuring units 95 be firmly attached to the measuring-unit supporting plate 91 by adhesion, ultrasonic welding, etc.

In the case of employing the measuring-unit connecting body 90, a plurality of measuring units 95 are first held in each of the measuring-unit supporting plates 91. Then, measuring-unit supporting plates 91 with the measuring units 95 therein are supported, for example, on the plate 40 shown in FIG. 4. In addition, a single measuring-unit supporting plate 91 can be fixed, for example, to the slide block 2 shown in FIG. 2. In this case, a plurality of measuring units 95 are supplied to the supporting plate 91 one by one. If the measurements are completed, then the measuring units 95 are removed from the supporting plate 91, and new measuring units 95 are supplied to the supporting plate 91.

The measuring-unit connecting body 90, among the aforementioned measuring-unit connecting bodies (8, 80, 90), is equipped with the measuring units 95 fixed so that they cannot be separated from one another. Therefore, the measuring-unit connecting body (measuring chip) becomes greater in size than a measuring chip consisting of a single measuring unit. Because of this, the accuracy of position in the surface plasmon resonance measuring apparatus can be easily obtained. In addition, the measuring-unit connecting body is easy to handle, because there is no need to handle small measuring units. Thus, the measuring-unit connecting body can make a contribution to an enhancement in the efficiency of the measuring operation.

In addition, the measuring-unit connecting body 90, among the aforementioned measuring-unit connecting bodies, is equipped with a plurality of measuring units 95. Therefore, with the supply or removal of a single measuring-unit connecting body, a plurality of measuring units can be supplied to or removed from the surface plasmon resonance measuring apparatus at a time. This is also able to contribute to an enhancement in the efficiency of the measuring operation.

Figure 11:
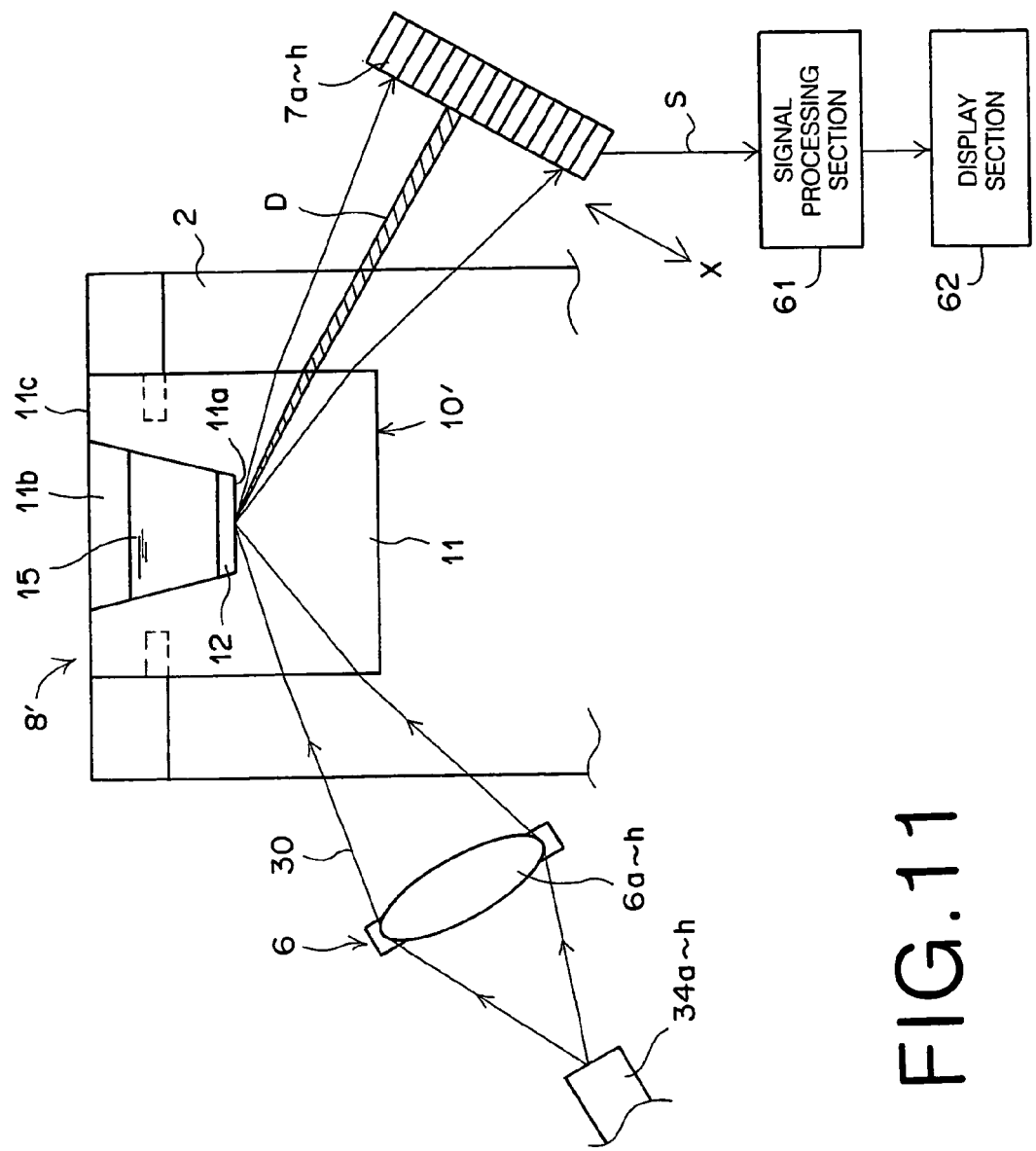
FIG. 11 is a side view showing the essential parts of a surface plasmon resonance measuring apparatus according to a second embodiment of the present invention.

FIG. 11 shows a surface plasmon resonance measuring apparatus constructed according to a second embodiment of the present invention. Note in the figure that the same reference numerals are applied to the same parts as those of FIG. 6, and that a description thereof is omitted unless particularly necessary (the same applies to all of the following descriptions).

In the surface plasmon resonance measuring apparatus shown in FIG. 11, the measuring unit 10' differs in construction from that shown in FIG. 6. That is, the measuring unit 10' differs in that the sensing substance 14 is removed from the measuring unit 10 shown in FIG. 6. The remaining construction is basically the same as in the surface plasmon resonance measuring apparatus shown in FIG. 6. As with the aforementioned case, a plurality of measuring units 10' are connected, and they are formed into a measuring-unit connecting body 8'.

In the case of employing the measuring units 10', the aforementioned specific incidence angle $\theta_{sp}$ similarly varies with the dielectric constant (i.e., refractive index) of a sample 15 in contact with a metal film. Therefore, a specific substance in the sample 15 can be quantitatively analyzed based on the specific incidence angle $\theta_{sp}$ detected.

In the surface plasmon resonance measuring apparatus of the second embodiment, as with the first embodiment, a plurality of measuring units 10' are integrated into a measuring-unit connecting body 8'. The measuring-unit connecting body 8' is held by a slide block 2, and light beams 30 are irradiated to the measuring units 10' at a time so that the measuring units 10' can be measured at the same time. Thus, the second embodiment is also capable of measuring a plurality of samples 15 in a short time.

Figure 12:
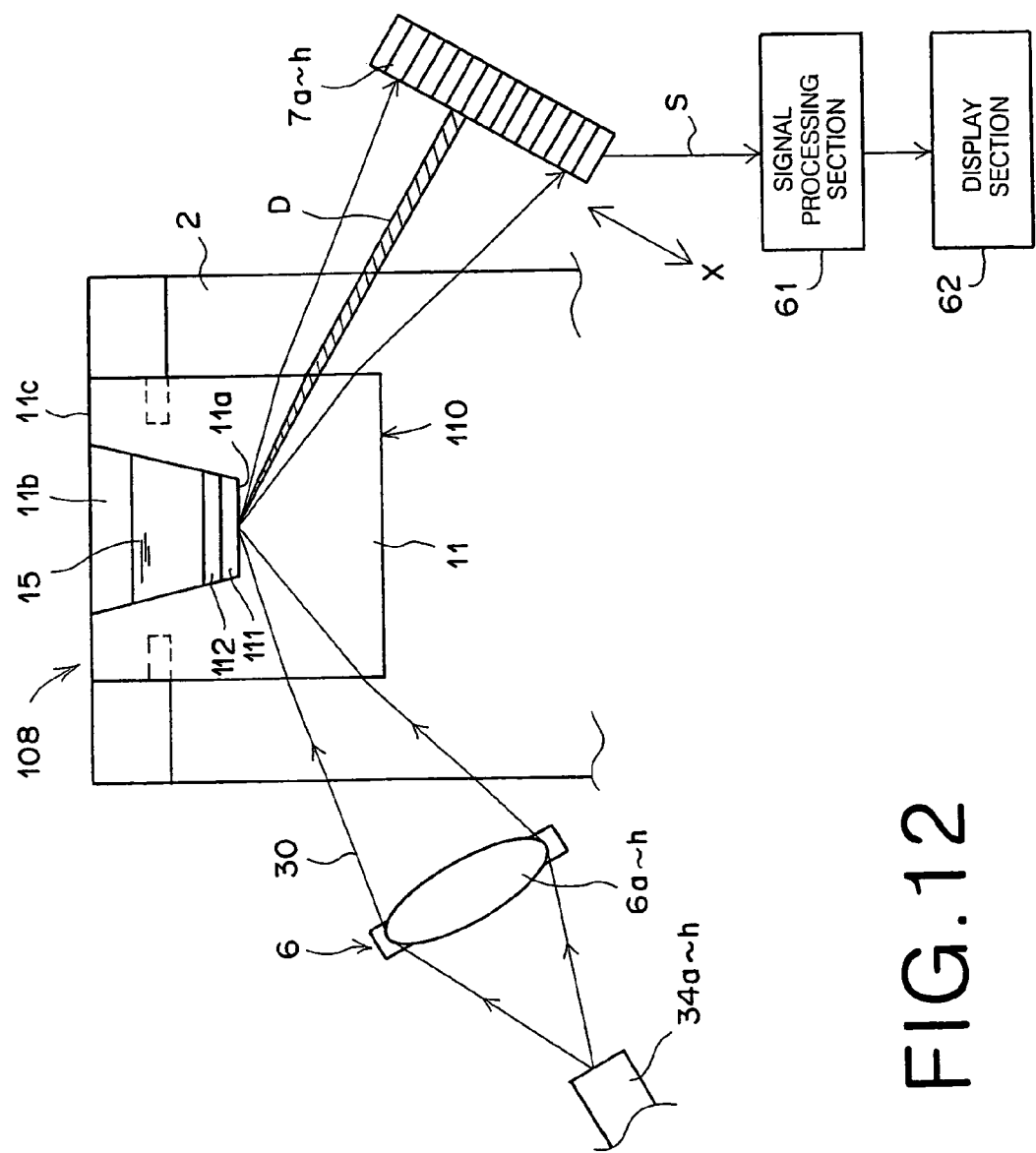
FIG. 12 is a side view showing the essential parts of a leaky mode sensor according to a third embodiment of the present invention.

FIG. 12 shows a measuring apparatus (leaky mode sensor), which utilizes ATR, constructed according to a third embodiment of the present invention. The leaky mode sensor of the third embodiment is equipped with a measuring-unit connecting body 108'. The measuring-unit connecting body 108' is used for supporting a plurality of measuring units 110 similar to the aforementioned measuring units 8 and 8'. A surface (bottom surface of a hole 11b) of a dielectric block 11 constituting the measuring unit 10 has a cladding layer 111 on which an optical waveguide layer 112 is formed.

The dielectric block 11 is formed, for example, from synthetic resin, or optical glass such as BK7, etc. The cladding layer 111 is formed into the shape of a thin film by employing a dielectric lower in refractive index than the dielectric block 11, or metal such as gold, etc. The optical waveguide layer 112 is also formed into a thin film by employing a dielectric higher in refractive index than the cladding layer 111, such as polymethylmethacrylate (PMMA). The thickness of the cladding layer 111 is, for example, 36.5 nm when it is formed from a thin gold film. The thickness of the optical waveguide layer 112 is, for example, about 700 nm when it is formed from PMMA.

In the leaky mode sensor of the third embodiment, if a convergent light beam 30 strikes the cladding layer 111 through the dielectric block 11 at incidence angles greater than an angle at which total internal reflection (TIR) occurs, the light beam 30 is totally reflected at the interface 11a between the dielectric block 11 and the cladding layer 111. However, the light with a specific wave number, incident on the optical waveguide layer 112 through the cladding layer 111 at a specific incidence angle, propagates through the optical waveguide layer 112 in a waveguide mode. If the waveguide mode is excited in this manner, the greater part of the incident light is confined within the optical waveguide layer 112, and consequently, ATR occurs in which the intensity of the light totally reflected at the interface 11a drops sharply.

The wave number of the light in the optical waveguide layer 112 depends on the refractive index of the sample 15 on the optical waveguide layer 112. Therefore, the refractive index of the sample 15 and the properties of the sample related to the refractive index can be analyzed by finding the above-mentioned specific incidence angle $\theta_{sp}$ at which ATR takes place. A signal processing section 61 is used for quantitatively analyzing a specific substance in the sample 15 according to the aforementioned principle, and the result of analysis is displayed on a display section 62.

In the leaky mode sensor of the third embodiment, as with the first embodiment, a plurality of measuring units 110 are integrated into the measuring-unit connecting body 108. The measuring-unit connecting body 108 is held by a slide block 2, and light beams 30 are irradiated to the measuring units 110 at a time so that the measuring units 110 can be measured at the same time. Thus, the third embodiment is also capable of measuring a great number of samples 15 in a short time.

Figure 13:
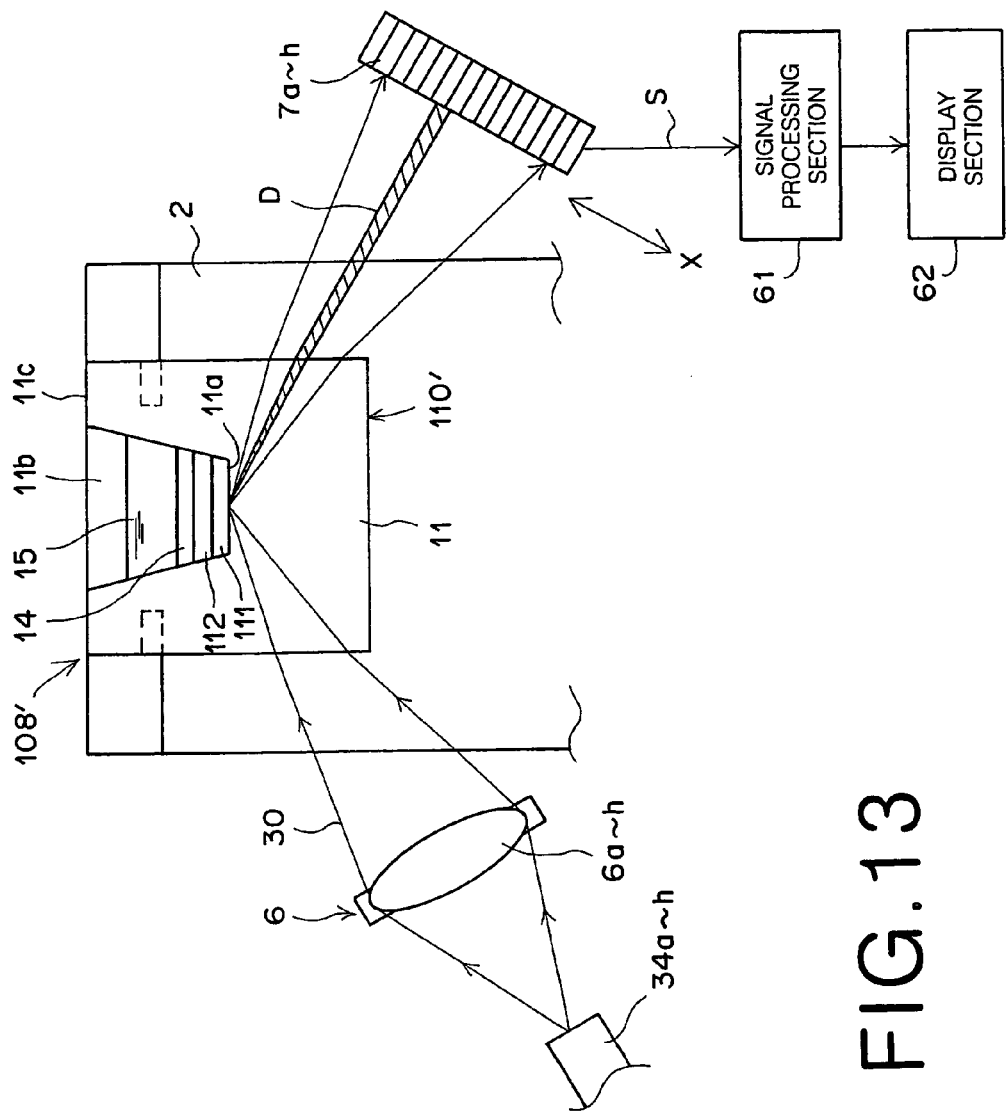
FIG. 13 is a side view showing the essential parts of a leaky mode sensor according to a fourth embodiment of the present invention.

FIG. 13 shows a measuring apparatus (leaky mode sensor), which utilizes ATR, constructed according to a fourth embodiment of the present invention. The leaky mode sensor of the fourth embodiment is equipped with a measuring-unit connecting body 108'. The measuring-unit connecting body 108' is used to support a plurality of measuring units 110' similar to the aforementioned measuring units 8 and 8'. The measuring unit 110' differs from the measuring unit 110 shown in FIG. 12 in that a sensing substance 14 is fixed on an optical waveguide layer 112.

The sensing substance 14, as with the sensing substance 14 in the measuring unit of FIG. 6, bonds with a specific substance in the sample 15. As an example of combination of the specific substance and the sensing substance 14, there are an antigen and an antibody. In that case, an antigen-antibody reaction can be detected based on the specific incidence angle $\theta_{sp}$ at which ATR occurs. The relationship between the incidence angle $\theta$ and light intensity I of the light beam 30 relative to the interface 11a is basically the same as that shown in FIG. 8. That is, the refractive index of the sensing substance 14 varies with the bond between the specific substance and the sensing substance 14, and the characteristic curve of FIG. 8 is horizontally shifted. Therefore, the antigen-antibody reaction can be detected based on the specific incidence angle $\theta_{sp}$.

In the aforementioned measuring-unit connecting bodies 8', 108, and 108, the measuring units are fixed so that they cannot be separated from one another. Each of the measuring-unit connecting bodies 8', 108, and 108 (measuring chips) is greater in size than a measuring chip consisting of a single measuring unit. Therefore, positional accuracy in the surface plasmon resonance measuring apparatus or leaky mode sensor can be easily obtained. In addition, the measuring-unit connecting bodies 8', 108, and 108 are easy to handle, because there is no need to handle small measuring units. Thus, the measuring-unit connecting bodies 8', 108, and 108 can make a contribution to an enhancement in the efficiency of the measuring operation. In addition, the measuring-unit connecting bodies 8', 108, and 108 are equipped with a plurality of measuring units. Therefore, with the supply or removal of a single measuring-unit connecting body, a plurality of measuring units can be supplied or removed. This is also able to contribute to an enhancement in the efficiency of the measuring operation.

Figure 14:
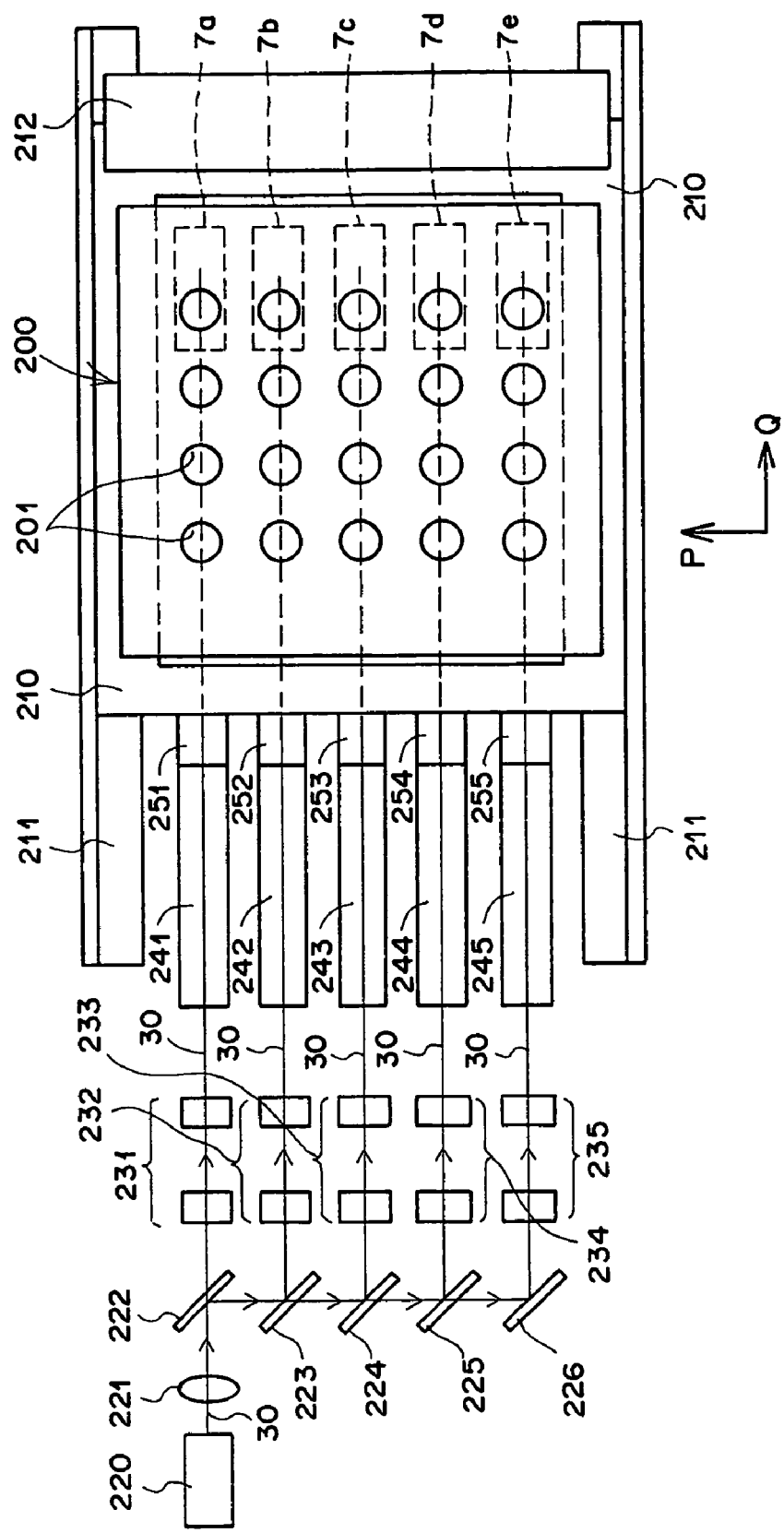
FIG. 14 is a plan view showing a surface plasmon resonance measuring apparatus according to a fifth embodiment of the present invention.
Figure 15:
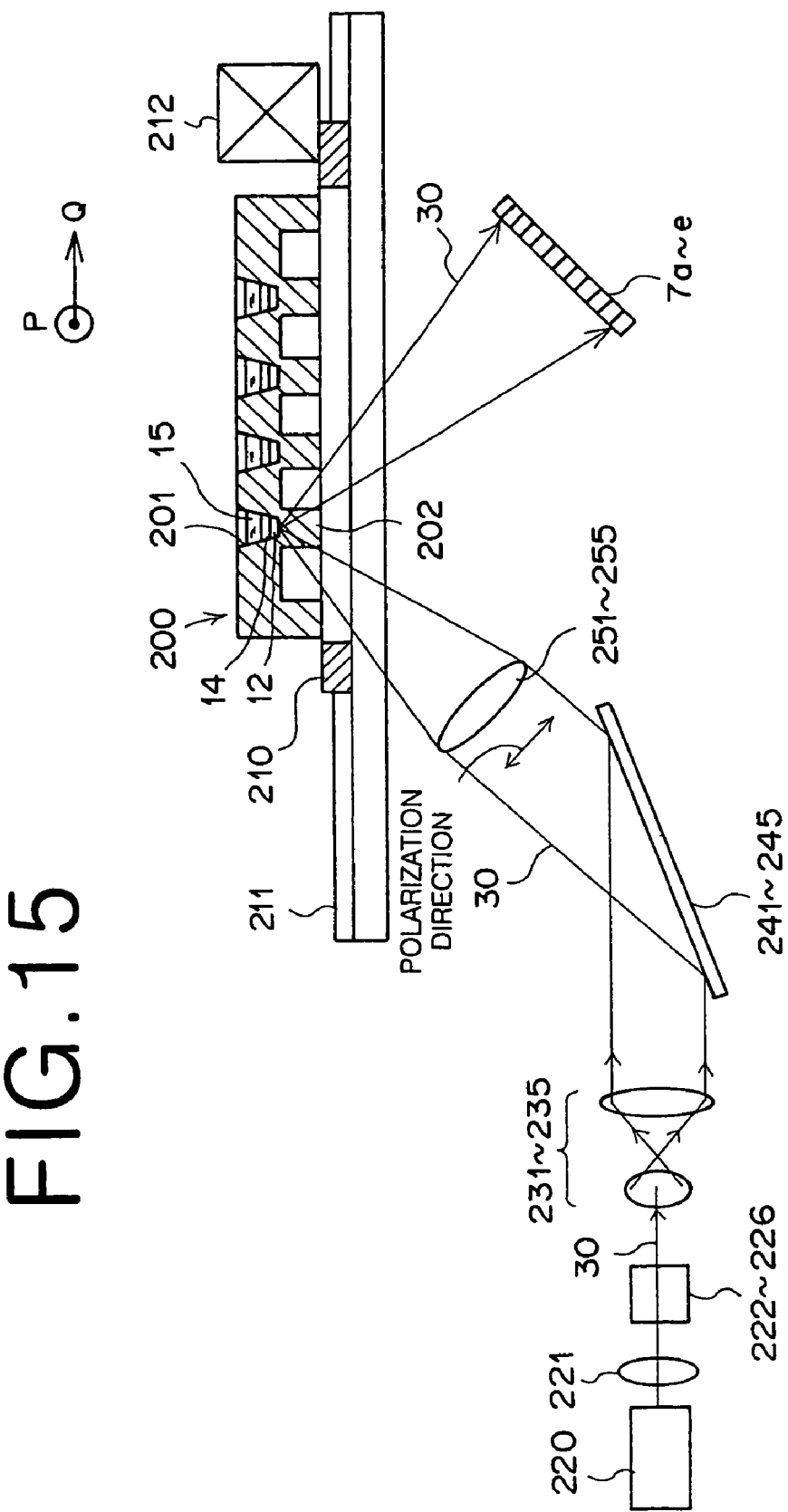
FIG. 15 is a part-sectional side view showing the surface plasmon resonance measuring apparatus of FIG. 14.

FIGS. 14 and 15 show a surface plasmon resonance measuring apparatus constructed according to a fifth embodiment of the present invention. The fifth embodiment employs a pallet 200 having a plurality of wells 201 for holding a sample 15. This pallet 200 constitutes the dielectric block and sample holding mechanism of the measuring unit and is also used as a supporting body for supporting the measuring units.

Figure 16:
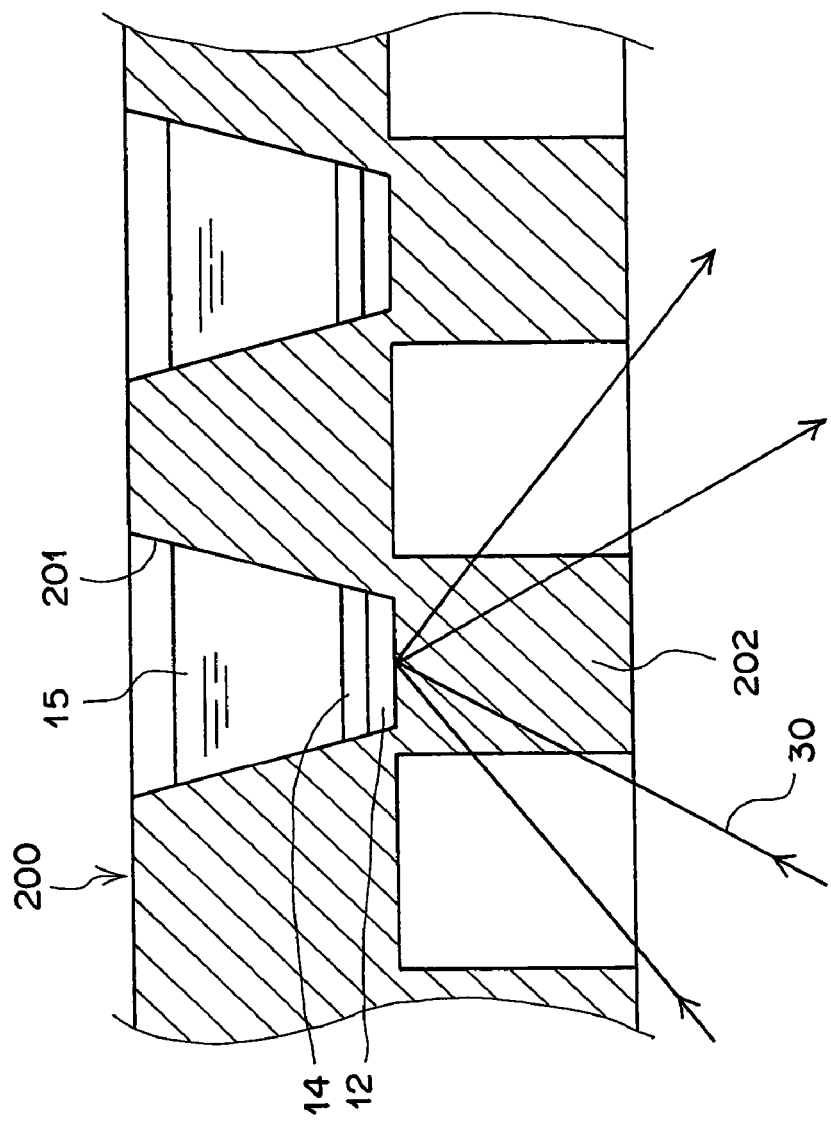
FIG. 16 is an enlarged side view showing a part of the surface plasmon resonance measuring apparatus of FIG. 14.

As shown in FIG. 16, the pallet 200 is formed from the same material as the transparent dielectric block 11 of FIG. 6. A metal film 12 and a sensing substance 14, similar to those shown in FIG. 6, are fixed in this order on the bottom of a well 201 formed in the shape of a truncated cone. The pallet 200 also has a dielectric block portion 202 extending downward from the bottom of each well 201. A measuring light beam 30 strikes the interface between the dielectric block portion 202 and the metal film 12. As shown in FIG. 14, a plurality of wells 202 are disposed in the transverse direction (indicated by arrow P) and the longitudinal direction (indicated by arrow Q).

The pallet 200 is placed at a predetermined position on a measuring-unit feed table 210. The measuring-unit feed table 210 is placed on a pair of rails 211, 211 extending in the direction of arrow P and is moved along the rails 211, 211 by drive means 212 mounted on the table 210. In the fifth embodiment, the measuring-unit feed table 210, rails 211, 211, and drive means 212 constitute measuring-unit feed means.

In the fifth embodiment, five light beams 30 strike the bottoms of a plurality of wells 201 (in this embodiment, five wells) disposed in the direction of arrow P, respectively. That is, the light beam 30 emitted divergently from a single laser light source 220 is collimated by a collimator lens 221 and is branched into 5 light beams 30 by half mirrors 222, 223, 224 and a mirror 226. The branched 5 light beams 30 strike the bottoms of the wells 201, i.e., the interfaces 12 between the dielectric block portions 202 and the metal films 12, respectively.

The five light beams 30 are expanded in diameter in the plane shown in FIG. 15 by cylindrical beam expanders 231, 232, 233, 234, and 235, respectively. The expanded light beams 30 are reflected by mirrors 241 to 245 and changed in direction. Then, the light beams 30 are condensed in the plane shown in FIG. 15 by cylindrical lenses 251 to 255, respectively. In this way, each light beam 30 strikes the interface between the dielectric block portion 202 and the metal film 12 at various incidence angles. Note that the laser light source 220 is oriented so that the light beam 30, which is a linearly polarized light beam, strikes the interface as a p-polarized light beam.

The light beams 30 totally reflected at the interfaces are detected by five photodetectors 7a to 7e similar to the photodetectors 7a to 7h of the first embodiment shown in FIG. 6. The outputs of the photodetectors 7a to 7e are processed in the same manner as in the first embodiment, and specific substances in the samples 15 are quantitatively analyzed.

In the fifth embodiment, as described above, the samples 15 held in the five wells 201 can be measured at the same time. If the measurements are completed, then the operation of the laser light source 220 is stopped. Next, the drive means 212 is operated, and the measuring-unit feed table 210 (i.e., pallet 200) is fed in the direction of arrow Q by a distance equal to the pitch between the wells 201. In this state, the laser light source 220 is again operated, and five new samples 15 are measured. In this manner, the fifth embodiment is capable of measuring a great number of samples within a short time with great efficiency.

While the fifth embodiment has employed only a single laser light source 220, the present invention may employ, for example, two light sources. In this case, the light beam from one of the two light sources can be branched into two light beams, while the light beam from the other can be branched into three light beams. In total, five light beams are obtainable.

Figure 17:
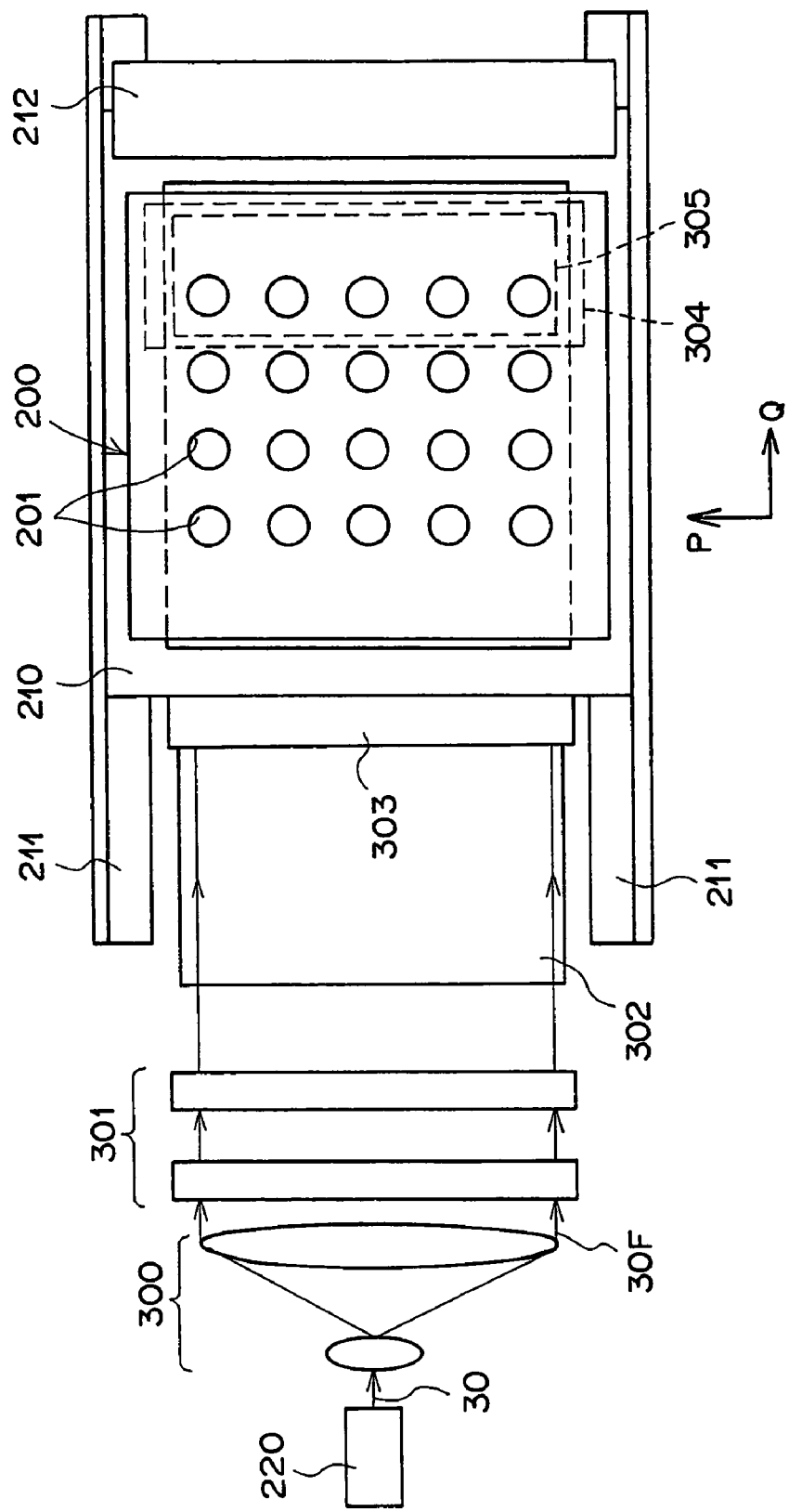
FIG. 17 is a plan view showing a surface plasmon resonance measuring apparatus according to a sixth embodiment of the present invention.
Figure 18:
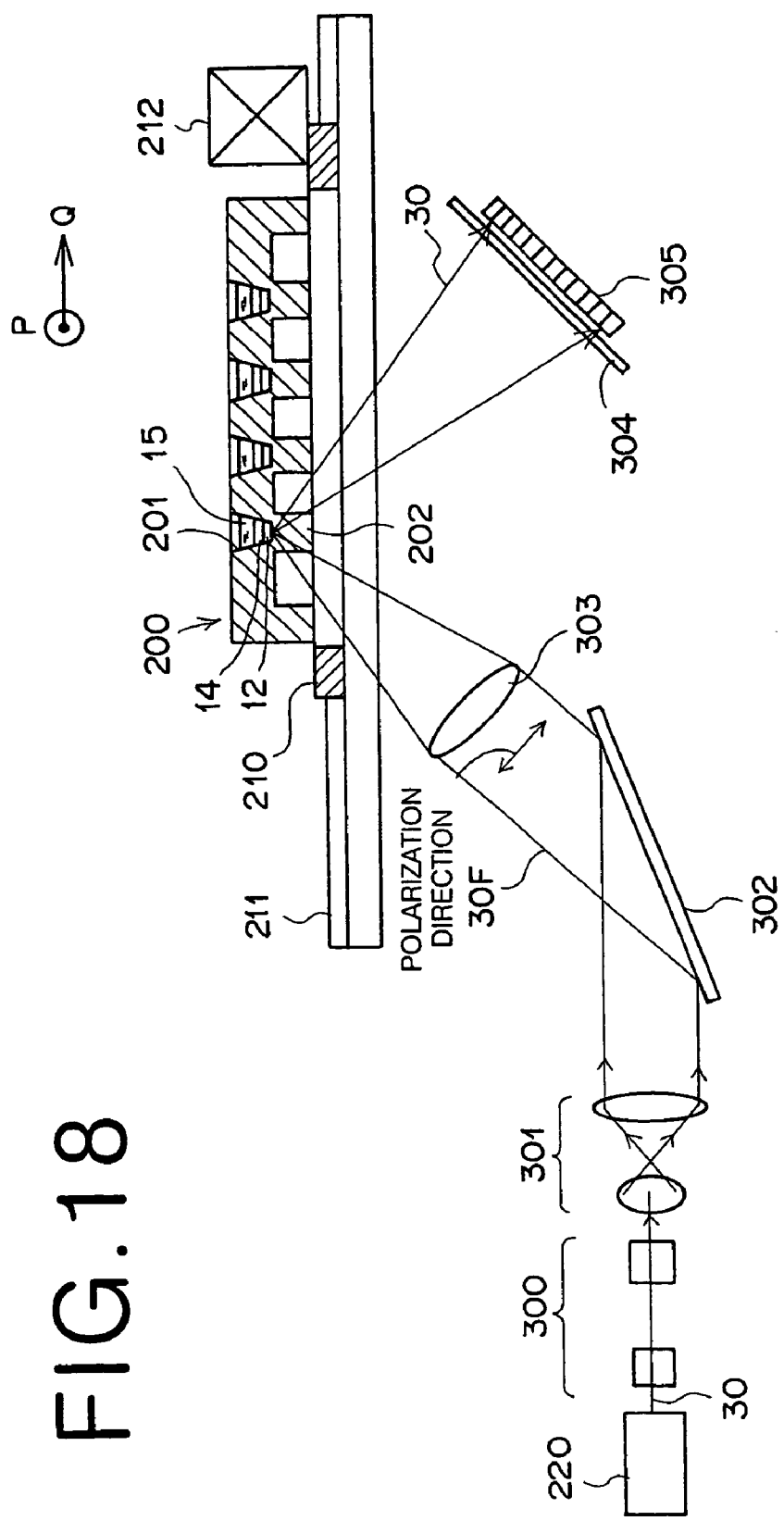
FIG. 18 is a part-sectional side view showing the surface plasmon resonance measuring apparatus of FIG. 17.

FIGS. 17 and 18 show a surface plasmon resonance measuring apparatus constructed according to a sixth embodiment of the present invention. The sixth embodiment employs the same pallet 200 as that employed in the fifth embodiment. In addition, the sixth embodiment is the same as the fifth embodiment in that a measuring-unit feed table 210, rails 211, 211, and drive means 212 are provided for feeding the pallet 200 by a distance equal to the pitch between wells 201.

In the sixth embodiment, a single flattened light beam 30F strikes the bottoms of a plurality of wells 201 (in this embodiment, five wells) disposed in the direction of arrow P, at the same time. That is, the light beam 30 emitted divergently from a single laser light source 220 is expanded in diameter in the plane shown in FIG. 17 by a cylindrical beam expander 300 and is flattened so that it can strike the bottoms of the five wells 201 at the same time.

The flattened light beam 30F is expanded in diameter in the plane shown in FIG. 18 by a cylindrical beam expander 301. The expanded light beam 30F is reflected by a large mirror 302 and changed in direction. Then, the light beam 30F is condensed in the plane shown in FIG. 18 by a cylindrical lens 303. In this way, the light beam 30F strikes the interfaces between the dielectric block portions 202 and the metal films 12 at various incidence angles. Note that the laser light source 220 is oriented so that the light beam 30F, which is a linearly polarized light beam, strikes the interfaces as a p-polarized light beam.

Figure 19:
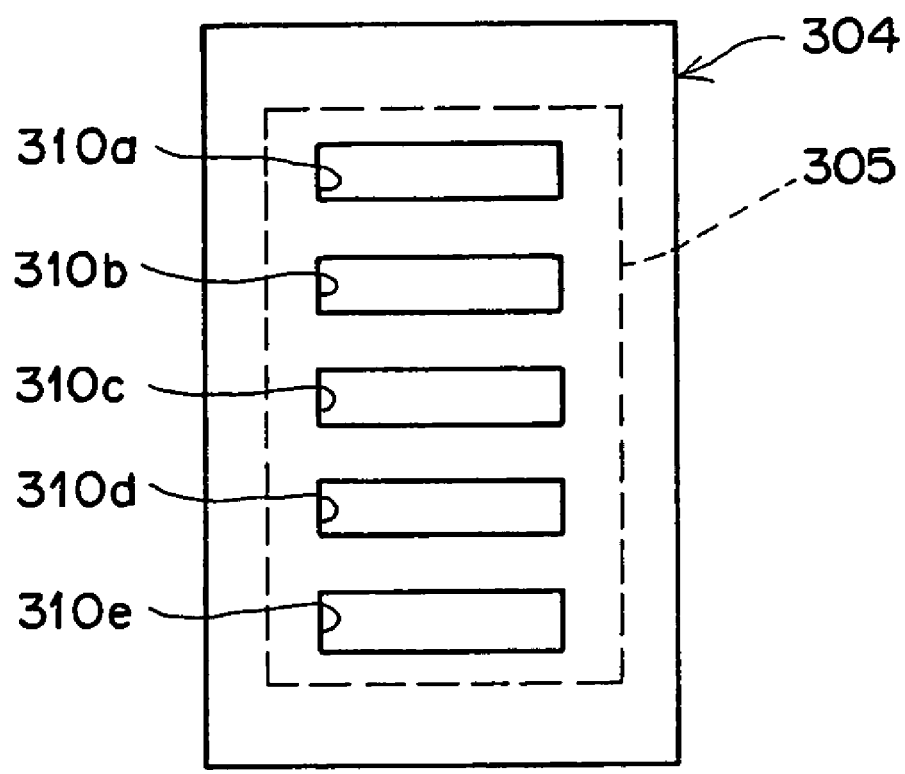
FIG. 19 is an enlarged plan view showing a part of the surface plasmon resonance measuring apparatus of FIG. 17.

The light beam 30F totally reflected at the interfaces is detected by a photodetector 305. The photodetector 305 consists of charge-coupled devices having a two-dimensional surface. As shown in FIG. 19, the front surface of the photodetector 305 is provided with a mask 304, which has five light-transmitting openings 310a to 310e. Among the components of the totally reflected light beam 30F, the components reflected at the interfaces of the five wells 201 are transmitted through the light-transmitting openings 310a to 310e and detected by the five different portions of the light-detecting surface of the photodetector 305. The outputs from the five different portions are independently processed in the same manner as in the first embodiment shown in FIG. 6, and specific substances in the samples 15 are quantitatively analyzed.

In the sixth embodiment, as described above, the samples 15 held in the five wells 201 can be measured at the same time. If the measurements are completed, then the measuring-unit pallet 200 is fed in the direction of arrow Q by a distance equal to the pitch between the wells 201. In this manner, the sixth embodiment is also capable of measuring a great number of samples within a short time with great efficiency.

While the sixth embodiment has employed only a single laser light source 220, the present invention may employ, for example, two light sources. In this case, the light beam from one of the two light sources can be flattened so that it strikes the bottoms of two wells 201, while the light beam from the other can be flattened so that it strikes the bottoms of three wells 201.

Figure 20:
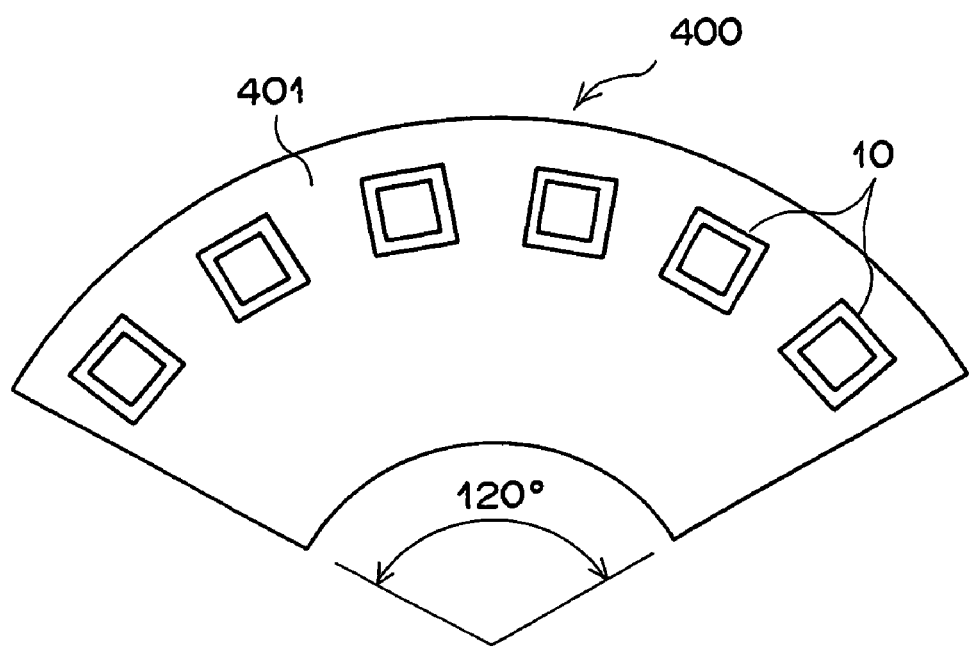
FIG. 20 is a plan view showing a measuring-unit connecting body according to a seventh embodiment of the present invention.

FIG. 20 shows a measuring-unit connecting body 400 that is a measuring chip according to a seventh embodiment of the present invention. As shown in the figure, the measuring-unit connecting body 400 consists of a fan-shaped unit supporting plate 401, which is obtained by trisecting an annular plate. As an example, the unit supporting plate 401 has six measuring units 10. These measuring units 10 are the same as the measuring unit 10 shown in FIG. 3, and are employed to measure surface plasmon resonance. The measuring units 10 are disposed along the circular arc of the fan-shaped unit supporting plate 401 with respect to the center.

The measuring-unit connecting body 400 can be applied to the aforementioned measuring apparatus in which a turntable with a plurality of measuring units along a circle is rotated by a predetermined angle at a time. For example, if three measuring-unit connecting bodies 400 are held at equiangular intervals by the turntable, eighteen measuring units 10 can be supported in total. In such a case, a light beam can be irradiated simultaneously to a plurality of measuring units 10 held by the turntable. In addition, if the turntable is rotated intermittently at intervals of an angle equal to the pitch between the measuring units 10, a light beam can be irradiated to the measuring units one by one.

Figure 21:
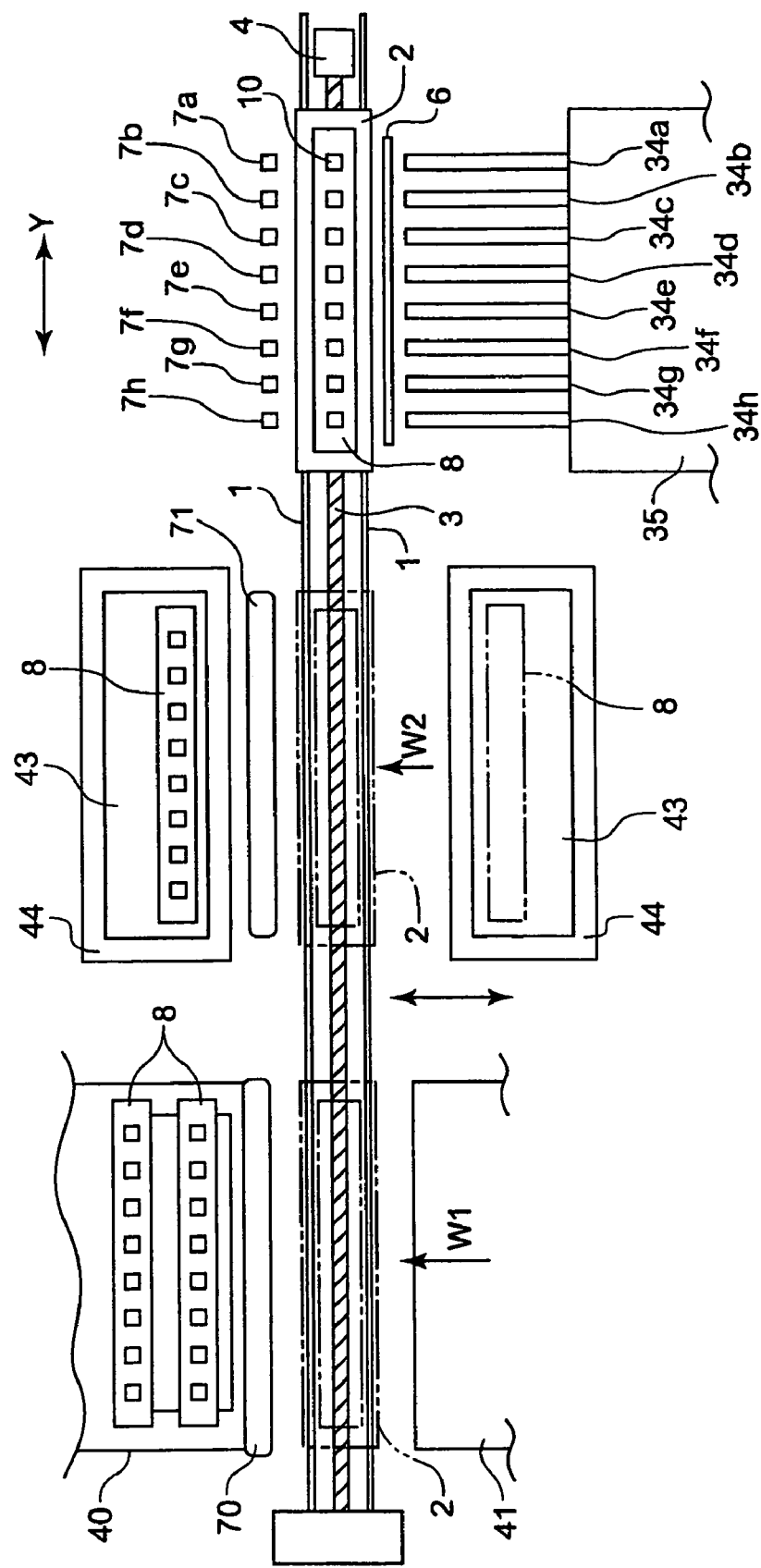
FIG. 21 is a plan view showing a surface plasmon resonance measuring apparatus according to an eighth embodiment of the present invention.

FIG. 21 shows a surface plasmon resonance measuring apparatus according to an eighth embodiment of the present invention. The surface plasmon resonance measuring apparatus of the eighth embodiment differs from the surface plasmon resonance measuring apparatus of the first embodiment in that preserving means is provided at the second standby position.

After a sample 15 is poured into a measuring unit 10, drift occurs for a while in a signal detected by the measuring apparatus. The major cause of a drift in the detected signal is that it takes time for the poured sample 15 to conform to the measuring unit, and meanwhile a fluctuation in temperature, etc., will occur in the measuring unit 10. Therefore, in the eighth embodiment, the samples 15 are poured into the measuring units 10, then the measuring units 10 are preserved under predetermined temperature control until a transient response time elapses, and the measuring-unit connecting body 8 during the transient response time, including the measuring units 10, is not allowed to occupy the measuring position.

At the aforementioned second standby position, there is provided a temperature adjustable incubator 44 (preserving means), and within this incubator 44, there is provided a mounting table 43.

Figure 22:
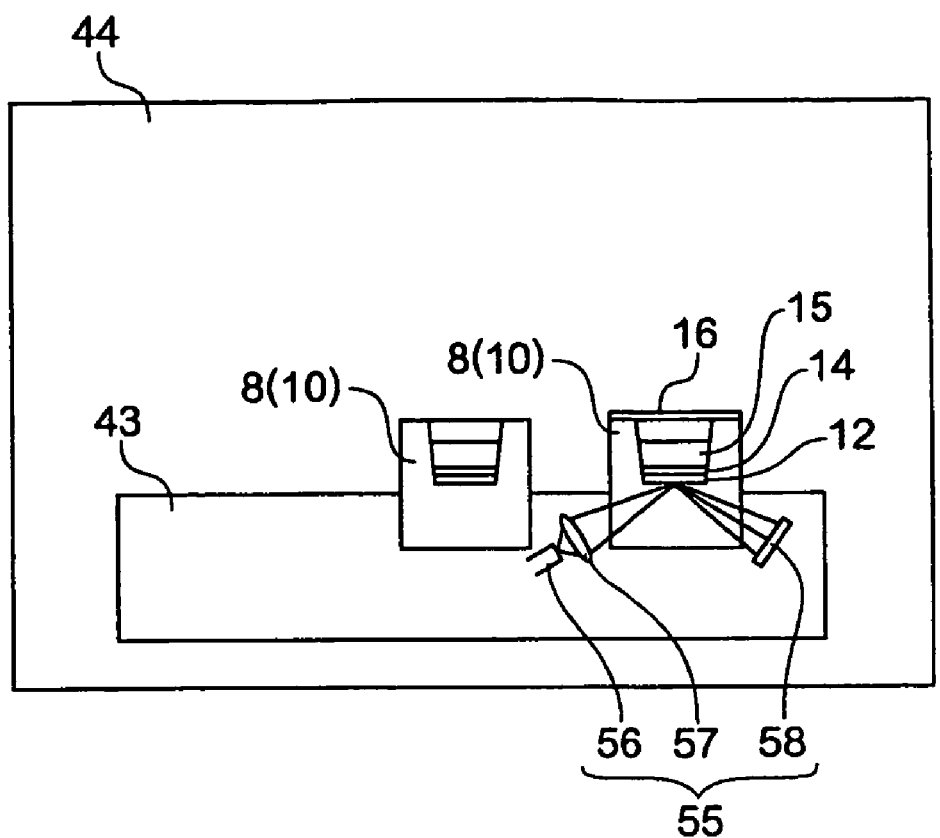
FIG. 22 is a schematic diagram showing the preservation means of the surface plasmon resonance measuring apparatus shown in FIG. 21.

In addition, to detect whether or not the measuring unit 10 preserved within the incubator 44 is in a transient response state, the incubator 44 is provided with a surface plasmon resonance measuring section 55 (state detection means), as shown in FIG. 22.

The surface plasmon resonance measuring section 55 is constructed of a semiconductor laser 56, a microlens 57, and a photodetector 58. The measuring section 55, as with the measuring section of the surface plasmon resonance measuring apparatus described in the above-mentioned first embodiment, utilizes surface plasmon resonance to analyze the physical properties of the sample 15. Since the sample 15 is normally poured into the 8 measuring units 10 of the measuring-unit connecting body 8 at the same time, the surface plasmon resonance measuring section 55 is used to measure at least one or more measuring units 10 of the measuring-unit connecting body 8 that is placed on the mounting table 43. For this reason, there may be provided a number of surface plasmon resonance measuring sections 55 that corresponds to the number of measuring-unit connecting bodies 8 placed on the mounting table 43, or the measuring-unit connecting body 8 may be movable so that it can measure one measuring-unit connecting body 8 at a time.

Furthermore, to prevent the sample 15 from evaporating during preservation, the measuring unit 10 may be provided with a cover 16.

In the eighth embodiment, as described above, the measuring-unit connecting body 8 is preserved within the incubator 44 until a transient response time elapses since the samples 15 were poured into the measuring units 10. After it is judged by the surface plasmon resonance measuring section 55 that the transient response time for the sample 15 has elapsed, the measuring-unit connecting body 8 is moved to the measuring position. Thus, there is no need to cause the measuring-unit connecting body 8 to wait for measurement at the measuring position until a transient response time for the sample 15 elapses, so it is possible to measure a great number of samples with great efficiency and accuracy.

While the eighth embodiment employs the state detection means for detecting the transient response state of the sample 15, the present invention is not limited to the detection means. For instance, a temperature sensor can be employed to detect a fluctuation in the temperature of the sample 15.

Figure 23:
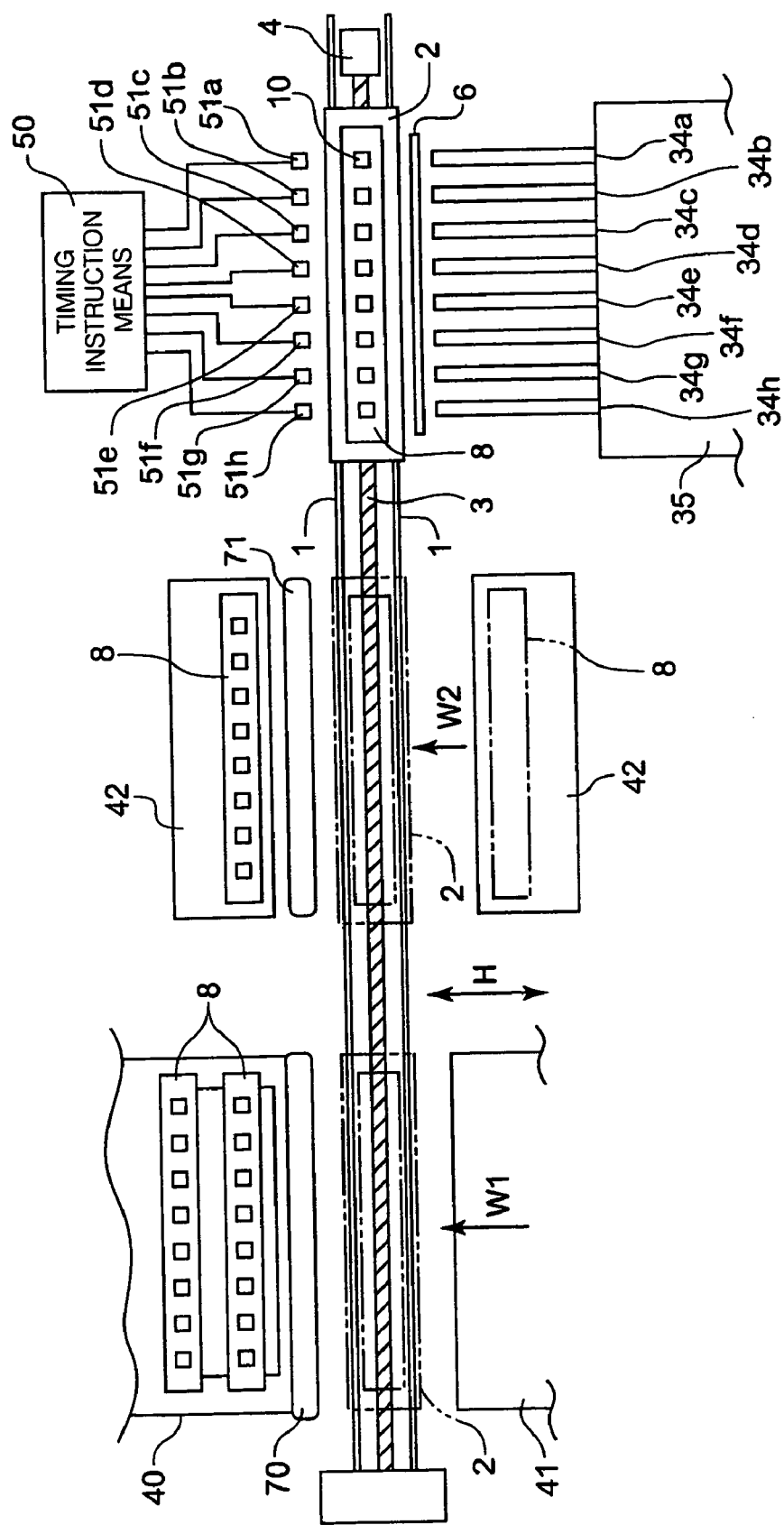
FIG. 23 is a plan view showing a surface plasmon resonance measuring apparatus according to a ninth embodiment of the present invention.

FIG. 23 shows a surface plasmon resonance measuring apparatus according to a ninth embodiment of the present invention. The surface plasmon resonance measuring apparatus of the ninth embodiment differs from the surface plasmon resonance measuring apparatus of the first embodiment in that photodetectors are provided with timing instruction means.

The photodetectors 51$a$ to 51$h$ of the ninth embodiment are connected to the timing instruction means 50 so that they can perform a detecting operation in synchronization with a timing instruction signal output from the timing instruction means 50. The timing instruction signal may be a clock signal, or a pulse signal that is output only during a detecting operation.

Such a construction makes it possible to simultaneously measure the samples 15 held in the 8 measuring units 10 of a measuring-unit connecting body 8, so that data correlated highly with time can be obtained between the measuring units 10 of the measuring-unit connecting body 8. Therefore, when data are compared or corrected between the measuring units 10 of the measuring-unit connecting body 8, the accuracy can be enhanced.

Figure 24:
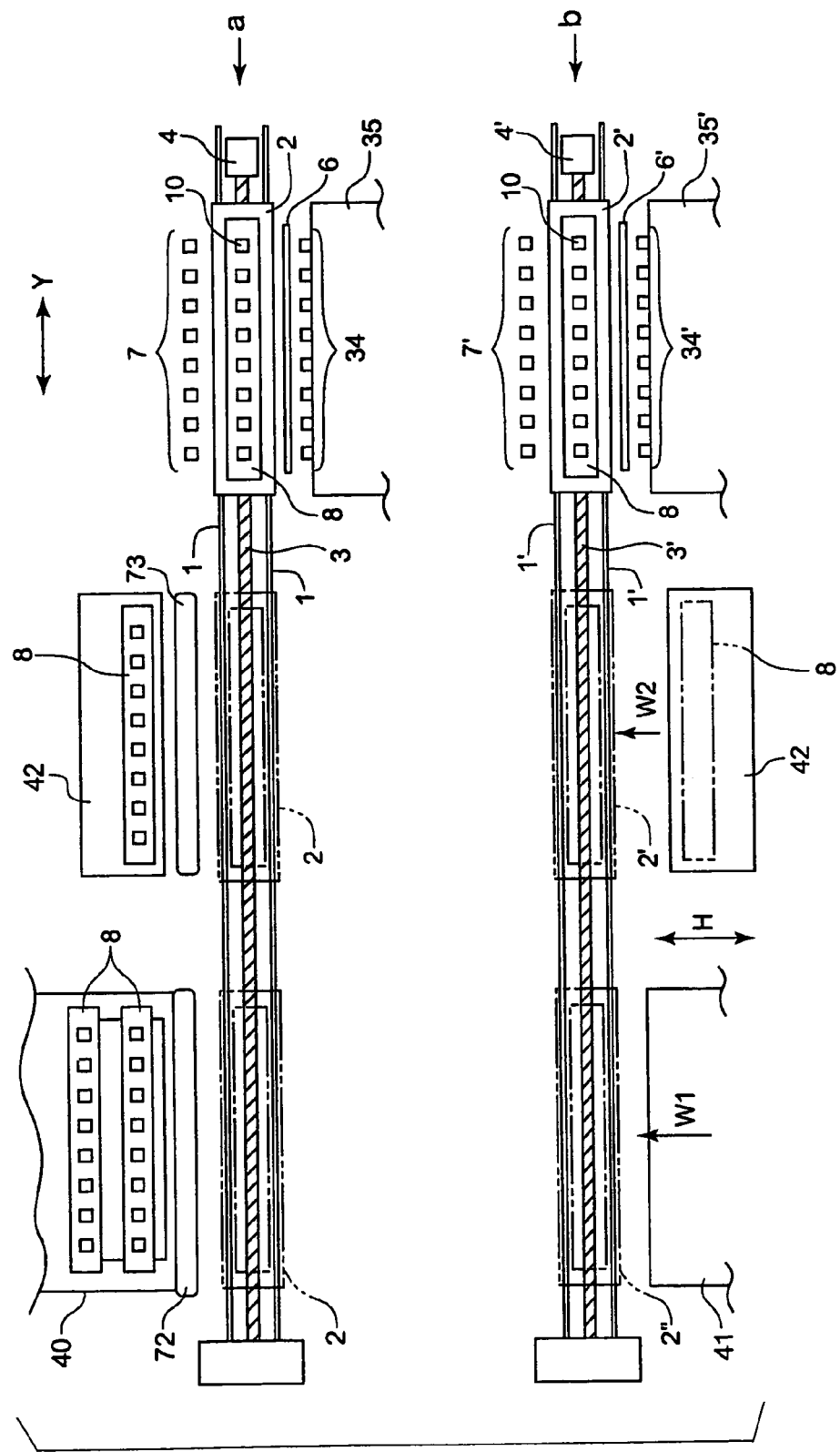
FIG. 24 is a plan view showing a surface plasmon resonance measuring apparatus according to a tenth embodiment of the present invention.

FIG. 24 shows a surface plasmon resonance measuring apparatus according to a tenth embodiment of the present invention. The surface plasmon resonance measuring apparatus of the ninth embodiment differs from the surface plasmon resonance measuring apparatus of the first embodiment in that it is provided with two measuring systems a and b.

The first measuring system a is constructed of guide rods 1, 1, a slide block 2, a fine screw 3, a pulse motor 4, a photodetector 7 (7$a$ to 7$h$ in FIG. 1), an optical fiber 34 (34$a$ to 34$h$ in FIG. 1), an optical coupler unit 35, a semiconductor laser 31 (not shown), and an optical system for causing a light beam from the semiconductor laser 31 to enter the optical coupler unit 35. Similarly, the second measuring system b is constructed of rods 1', 1', a slide block 2', a fine screw 3', a pulse motor 4', a photodetector 7', an optical fiber 34', an optical coupler unit 35', a semiconductor laser 31', and an optical system for causing a light beam from the semiconductor laser 31' to enter the optical coupler unit 35'. In addition, the supply and removal of the measuring-unit connecting body 8 with respect to the slide blocks 2 and 2' are performed by measuring-unit supply mechanisms 72 and 73.

In the surface plasmon resonance measuring apparatus of the ninth embodiment, the same measurement may be made with the two measuring systems. As described below, different measurements may also be made with the two measuring systems.

In the case of making different measurements with the two measuring systems, for example, the first measuring system measures the quantity of a sensing substance 14 fixed on a metal film 12 without pouring the sample 15 into the measuring unit 10, and the second measuring system measures the reaction between the sensing substance 14 and the sample 15 after the sample 15 is poured into the measuring unit 10 having the sensing substance 14 measured by the first measuring system. The result obtained by the second measuring system is corrected with the result obtained by the first measuring system. In this manner, the quantity of reaction of the sample 15 per a unit sensing substance weight can be measured.

Such a measurement can be efficiently made, if the first measuring system makes a measurement of a first measuring-unit connecting body 8, then the first measuring system makes a measurement of a second measuring-unit connecting body 8 and, at the same time, the second measuring system makes a measurement of the first measuring-unit connecting body 8.

Thus, the tenth embodiment is also able to make measurements at the same time with the two measuring systems and is therefore able to measure a great number of samples within a short time with great efficiency.

Figure 25:
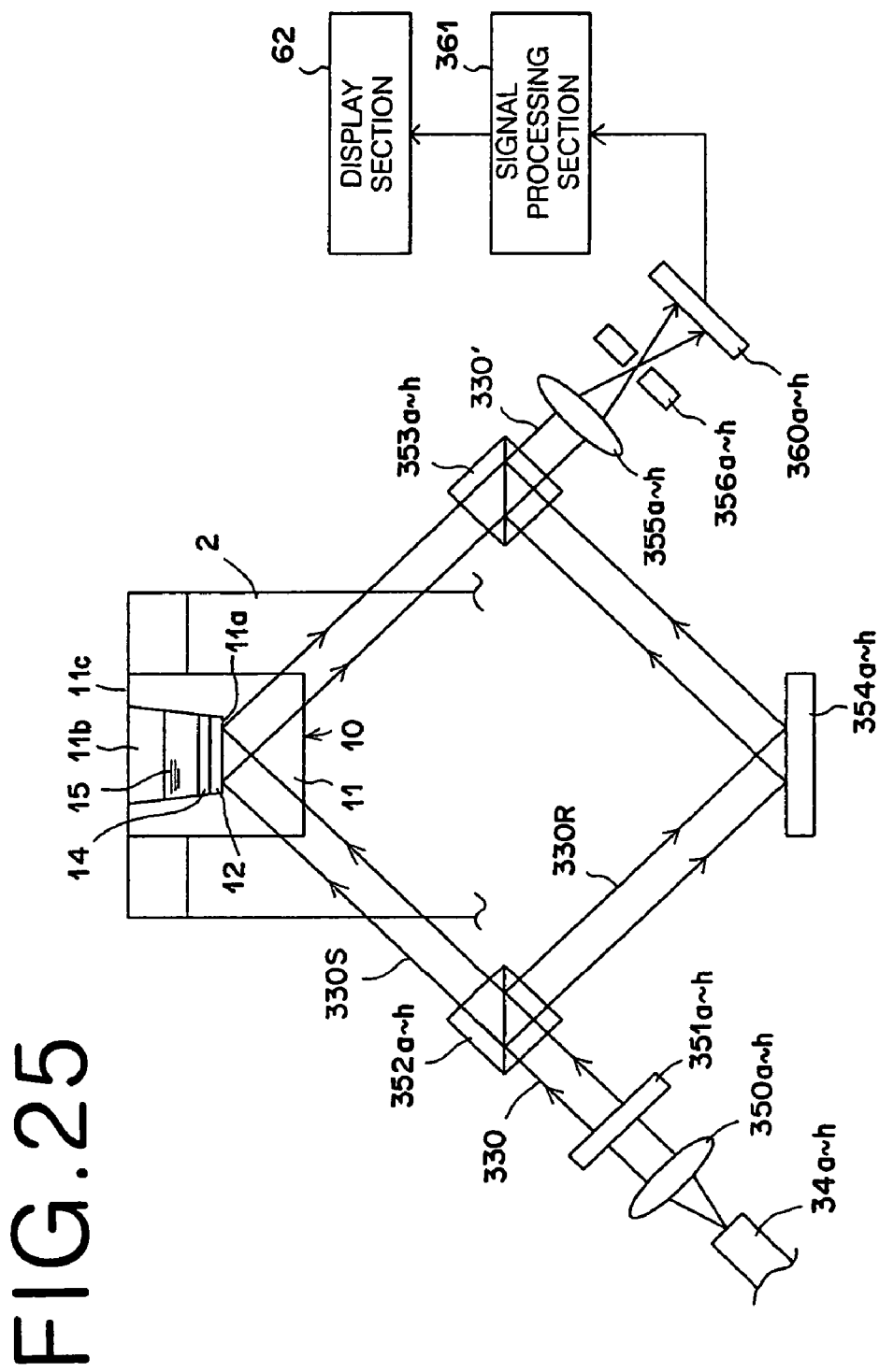
FIG. 25 is a plan view showing a surface plasmon resonance measuring apparatus according to an eleventh embodiment of the present invention.

FIG. 25 shows a surface plasmon resonance measuring apparatus according to an eleventh embodiment of the present invention. In this embodiment, a method of analyzing a sample is different from that of the first embodiment.

As shown in the figure, the surface plasmon resonance measuring apparatus of the eleventh embodiment is equipped with optical fibers 34a to 34h and charge-coupled devices 360a to 360h, which are disposed across a slide block 2 at measuring positions. The measuring apparatus is further equipped with collimator lenses 350a to 350h, an optical interference system, condenser lenses 355a to 355h, and apertures 356a to 356h.

The optical interference system is constructed of polarizing filters 351a to 351h, half mirrors 352a to 352h, mirrors 353a to 353h, and mirrors 354a to 354h. The charge-coupled devices 360a to 360h are connected to a signal processing section 361, which is in turn connected to a display section 62.

A description will hereinafter be given of the measurement of a sample in the surface plasmon resonance measuring apparatus of the eleventh embodiment. Although a description will be given of one of the eight measuring units 10 of a measuring-unit connecting body 8 which is aligned with the optical fiber 34a and charge-coupled device 360a, the remaining units 10 can be measured in the same manner.

As described in the first embodiment, the semiconductor laser 31 is driven and light beam 330 is emitted divergently from the end face of the optical fiber 34a. The light beam 330 is collimated by the collimator lens 350a and enters the polarizing filter 351a. The light beam 330 is transmitted through the polarizing filter 351a so that it enters an interface 11a as a p-polarized light beam. The light beam 330 from the polarizing filter 351a is split into a reference light beam 330R and a light beam 330S by the half mirror 352a. The light beam 330S strikes the interface 11a. The light beam 330S totally reflected at the interface 11a, and the reference light beam 330R reflected at the mirror 354a, are synthesized into a light beam 330' by the half mirror 353a. The synthesized light beam 330' is condensed by the condenser lens 355a. The light beam 330' is passed through the aperture 356a and detected by the charge-coupled device 360a. At this time, the light beam 330' detected by the charge-coupled device 360a produces an interference fringe according to the state of the interference between the light beam 330S and the reference light beam 330R.

A sensing substance 14 fixed on the surface of the metal film 12 bonds with a specific substance in the sample 15. As an example of combination of the specific substance and the sensing substance 14, there are an antigen and an antibody. In that case, an antigen-antibody reaction can be detected by measuring the sample 15 continuously after it is poured into the measuring unit 10, and then detecting a change in the interference fringe detected by the charge-coupled device 360a. That is, if the refractive index of the sensing substance 14 changes according to the bond between the specific substance and the sensing substance 14, the state of interference will change when the light beam 330S and the reference light beam 330R are synthesized by the half mirror 353a. Therefore, the antigen-antibody reaction can be detected according to a change in the interference. In this case, both the sample 15 and the sensing substance 14 are samples that are analyzed.

The signal processing section 361 detects the above-mentioned reaction, based on the aforementioned principle. The result of detection is displayed on the display section 62.

The measuring operation described above is likewise performed on the remaining seven measuring units 10 in parallel with the aforementioned one measuring unit 10. That is, the samples 15 held in the 8 measuring units 10 are measured at the same time. Note that the irradiation of the light beam 330 and detection of the antigen-antibody reaction with respect to the 8 measuring units 10 do not always need to be performed in a strictly simultaneous manner. The start times or end times may be slightly different from one another.

Thus, according to the eleventh embodiment, it becomes possible to measure a great number of samples in a short time, because the measurements of the samples 15 of the eight measuring units 10 can be performed simultaneously or at nearly the same time.

Note that the signal processing section 361 may be provided for each of the eight charge-coupled devices 360a to 360h, or one signal processing section may be shared by the eight charge-coupled devices 360a to 360h. In this case, light-quantity detection signals S output from the charge-coupled devices 360a to 360h are serially processed.

While the present invention has been described with reference to the preferred embodiments thereof, the invention is not to be limited to the details given herein, but may be modified within the scope of the invention hereinafter claimed.

What is the claimed is:

1. A measuring chip for use in a measuring apparatus constructed of a light source for emitting a light beam, an optical incidence system for making said light beam enter said dielectric block at an angle of incidence so that a total internal reflection condition is satisfied at an interface between said dielectric block and said thin film layer, and photodetection means for measuring the intensity of said light beam totally reflected at said interface, said measuring chip comprising:
   a dielectric block; and
   a thin film layer, formed on a surface of said dielectric block, which is contacted with a sample;
   wherein a plurality of measuring units, each of which comprise said dielectric block and said thin film, are arranged in a row and integrated;
   wherein
   the dielectric blocks of said integrated measuring units are discretely formed; and
   the discrete dielectric blocks are connected together and integrated by a connecting member.

2. A measuring chip as defined in claim 1, further comprising a sample holding mechanism for holding said sample on said thin film layer.

3. A measuring chip as defined in claim 1, wherein said dielectric block is formed from either glass or transparent resin.

4. A measuring chip as defined in claim 1, wherein a sensing substance that exhibits a bonding reaction with a specific substance in said sample is fixed on said thin film layer.

5. A measuring chip for use in a measuring apparatus constructed of a light source for emitting a light beam, an optical incidence system for making said light beam enter a dielectric block at an angle of incidence so that total internal reflection conditions are satisfied at an interface between said dielectric block and a thin film layer, and photodetection means for measuring the intensity of said light beam totally reflected at said interface, said measuring chip comprising:
   a plurality of measuring units, each of which comprises said dielectric block, said thin film layer, and a sample holding mechanism for holding a sample on the thin film layer; wherein:

said plurality of measuring units are arranged in a line and integrated; and each of the sample holding mechanisms of the plurality of measuring units holds a different sample.

6. A measuring chip as defined in claim 5, wherein:

the dielectric blocks of said integrated measuring units are discretely formed; and the discrete dielectric blocks are connected together and integrated by a connecting member.

7. A measuring chip as defined in claim 5, wherein:

the dielectric blocks of said integrated measuring units are formed from a single member.

8. A measuring chip as defined in claim 5, wherein:

said dielectric block is formed from either glass or transparent resin.

9. A measuring chip as defined in claim 5, wherein:

a sensing substance that exhibits a bonding reaction with a specific substance in said sample is fixed on said thin film layer.

* * * * *